US009610021B2

(12) United States Patent  
Dvorsky et al.

(10) Patent No.: US 9,610,021 B2  
(45) Date of Patent: Apr. 4, 2017

(54) METHOD FOR EVALUATING BLUSH IN MYOCARDIAL TISSUE

(71) Applicant: NOVADAQ TECHNOLOGIES INC., Mississauga (CA)

(72) Inventors: Peter Dvorsky, Toronto (CA); David Mark Henri Goyette, Mississauga (CA); T. Bruce Ferguson, Jr., Raleigh, NC (US); Cheng Chen, Greenville, NC (US)

(73) Assignee: Novadaq Technologies Inc., Mississauga (CA)

( * ) Notice: Subject to any disclaimer, the term of this patent is extended or adjusted under 35 U.S.C. 154(b) by 0 days.

(21) Appl. No.: 14/598,832

(22) Filed: Jan. 16, 2015

(65) Prior Publication Data

US 2015/0196208 A1   Jul. 16, 2015

Related U.S. Application Data

(60) Division of application No. 13/850,063, filed on Mar. 25, 2013, now Pat. No. 8,965,488, which is a division (Continued)

(51) Int. Cl.
*A61B 5/0275* (2006.01)
*G06T 7/40* (2006.01)

(Continued)

(52) U.S. Cl.
CPC .......... *A61B 5/0275* (2013.01); *A61B 5/0059* (2013.01); *A61B 5/0261* (2013.01);

(Continued)

(58) Field of Classification Search
CPC . A61B 2572/02; A61B 5/0059; A61B 5/0261; A61B 5/0275; A61B 5/489;

(Continued)

(56) References Cited

U.S. PATENT DOCUMENTS 4,109,647 A   8/1978   Stern et al.
4,162,405 A   7/1979   Chance et al.

(Continued)

FOREIGN PATENT DOCUMENTS

AT   409451 B   8/2002
CA   2212257 A1   8/1996

(Continued)

OTHER PUBLICATIONS

Azuma et al. "Detection of Skin Perforators by Indocyanine Green Fluorescence Nearly Infrared Angiography." Oct. 2008, pp. 1062-1067.

(Continued)

*Primary Examiner* — Michael Rozanski
(74) *Attorney, Agent, or Firm* — Morrison & Foerster LLP

(57) ABSTRACT

Vessel perfusion and myocardial blush are determined by analyzing fluorescence signals obtained in a static region-of-interest (ROI) in a collection of fluorescence images of myocardial tissue. The blush value is determined from the total intensity of the intensity values of image elements located within the smallest contiguous range of image intensity values containing a predefined fraction of a total measured image intensity of all image elements within the ROI. Vessel (arterial) peak intensity is determined from image elements located within the ROI that have the smallest contiguous range of highest measured image intensity values and contain a predefined fraction of a total measured image intensity of all image elements within the ROI. Cardiac function can be established by comparing the time differential between the time of peak intensity in a blood vessel and that in a region of neighboring myocardial tissue both pre and post procedure.

7 Claims, 12 Drawing Sheets

Related U.S. Application Data of application No. 12/841,659, filed on Jul. 22, 2010, now Pat. No. 8,406,860, which is a continuation-in-part of application No. PCT/CA2009/000073, filed on Jan. 23, 2009.

(60) Provisional application No. 61/023,818, filed on Jan. 25, 2008, provisional application No. 61/243,688, filed on Sep. 18, 2009.

(51) Int. Cl.

| | | |
|---|---|---|
| *G06T 7/00* | (2006.01) | |
| *A61B 5/00* | (2006.01) | |
| *A61B 6/00* | (2006.01) | |
| *A61B 5/026* | (2006.01) | |
| *A61M 5/00* | (2006.01) | |
| *G06T 7/20* | (2017.01) | |

(52) U.S. Cl.
CPC .......... *A61B 5/489* (2013.01); *A61B 5/7225* (2013.01); *A61B 6/503* (2013.01); *A61M 5/007* (2013.01); *G06T 7/0012* (2013.01); *G06T 7/0083* (2013.01); *G06T 7/0085* (2013.01); *G06T 7/204* (2013.01); *G06T 7/408* (2013.01); *A61B 6/504* (2013.01); *A61B 6/507* (2013.01); *A61B 2576/02* (2013.01); *G06T 2207/10064* (2013.01); *G06T 2207/30104* (2013.01)

(58) Field of Classification Search
CPC ....... A61B 5/7225; A61B 6/503; A61B 6/504; A61B 6/507; A61M 5/007; G06T 2207/10064; G06T 2207/30104; G06T 7/0012; G06T 7/0083; G06T 7/0085; G06T 7/204; G06T 7/408
See application file for complete search history.

(56) References Cited

U.S. PATENT DOCUMENTS

| | | | |
|---|---|---|---|
| 4,200,801 A | 4/1980 | Schuresko | |
| 4,394,199 A | 7/1983 | Barnhard, IV et al. | |
| 4,473,841 A | 9/1984 | Murakoshi et al. | |
| 4,532,918 A | 8/1985 | Wheeler | |
| 4,541,438 A | 9/1985 | Parker et al. | |
| 4,556,057 A | 12/1985 | Hiruma et al. | |
| 4,619,249 A | 10/1986 | Landry | |
| 4,718,417 A | 1/1988 | Kittrell et al. | |
| 4,719,508 A | 1/1988 | Sasaki et al. | |
| 4,768,513 A | 9/1988 | Suzuki | |
| 4,773,097 A | 9/1988 | Suzaki et al. | |
| 4,774,568 A | 9/1988 | Matsuo | |
| 4,786,813 A | 11/1988 | Svanberg et al. | |
| 4,805,597 A | 2/1989 | Iwakoshi | |
| 4,815,848 A | 3/1989 | Hadeishi | |
| 4,821,117 A | 4/1989 | Sekiguchi | |
| 4,827,908 A | 5/1989 | Matsuo | |
| 4,852,579 A | 8/1989 | Gilstad et al. | |
| 4,858,001 A | 8/1989 | Milbank et al. | |
| 4,860,731 A | 8/1989 | Matsuura | |
| 4,867,137 A | 9/1989 | Takahashi | |
| 4,868,647 A | 9/1989 | Uehara et al. | |
| 4,900,934 A | 2/1990 | Peeters et al. | |
| 4,930,516 A | 6/1990 | Alfano et al. | |
| 4,938,205 A | 7/1990 | Nudelman | |
| 4,957,114 A | 9/1990 | Zeng et al. | |
| 4,993,404 A | 2/1991 | Lane | |
| 4,995,396 A | 2/1991 | Inaba et al. | |
| 4,995,398 A | 2/1991 | Turnidge | |
| 4,998,972 A | 3/1991 | Chin et al. | |
| 5,003,977 A | 4/1991 | Suzuki et al. | |
| 5,042,494 A | 8/1991 | Alfano | |
| 5,071,417 A | 12/1991 | Sinofsky | |
| 5,078,150 A | 1/1992 | Hara et al. | |
| 5,090,400 A | 2/1992 | Saito | |
| 5,091,652 A | 2/1992 | Mathies et al. | |
| 5,115,137 A | 5/1992 | Andersson-Engels et al. | |
| 5,117,466 A | 5/1992 | Buican et al. | |
| 5,125,404 A | 6/1992 | Kittrell et al. | |
| 5,131,398 A | 7/1992 | Alfano et al. | |
| 5,134,662 A | 7/1992 | Bacus et al. | |
| 5,165,079 A | 11/1992 | Schulz-Hennig | |
| 5,178,616 A | 1/1993 | Uemiya et al. | |
| 5,196,928 A | 3/1993 | Karasawa et al. | |
| 5,214,503 A | 5/1993 | Chiu et al. | |
| 5,225,883 A | 7/1993 | Carter et al. | |
| 5,255,087 A | 10/1993 | Nakamura et al. | |
| 5,279,298 A | 1/1994 | Flower | |
| 5,318,023 A | 6/1994 | Vari et al. | |
| 5,318,024 A | 6/1994 | Kittrell et al. | |
| 5,318,869 A | 6/1994 | Hashimoto et al. | |
| 5,340,592 A | 8/1994 | Goodrich, Jr. et al. | |
| 5,361,769 A | 11/1994 | Nilsson | |
| 5,365,057 A | 11/1994 | Morley et al. | |
| 5,371,355 A | 12/1994 | Wodecki | |
| 5,375,603 A | 12/1994 | Feiler | |
| 5,377,676 A | 1/1995 | Vari et al. | |
| 5,377,686 A | 1/1995 | O'Rourke et al. | |
| 5,394,199 A | 2/1995 | Flower | |
| 5,419,323 A | 5/1995 | Kittrell et al. | |
| 5,420,628 A | 5/1995 | Poulsen et al. | |
| 5,421,337 A | 6/1995 | Richards-Kortum et al. | |
| 5,421,339 A | 6/1995 | Ramanujam et al. | |
| 5,424,841 A | 6/1995 | Van Gelder et al. | |
| 5,430,476 A | 7/1995 | Häfele et al. | |
| 5,437,274 A | 8/1995 | Khoobehi et al. | |
| 5,438,989 A | 8/1995 | Hochman et al. | |
| 5,453,448 A | 9/1995 | Narciso, Jr. | |
| 5,465,718 A | 11/1995 | Hochman et al. | |
| 5,496,369 A | 3/1996 | Howard, III | |
| 5,507,287 A | 4/1996 | Palcic et al. | |
| 5,514,127 A | 5/1996 | Shanks | |
| 5,519,534 A | 5/1996 | Smith et al. | |
| 5,576,013 A | 11/1996 | Williams et al. | |
| 5,590,660 A | 1/1997 | MacAulay et al. | |
| 5,623,930 A | 4/1997 | Wright et al. | |
| 5,627,907 A | 5/1997 | Gur et al. | |
| 5,647,368 A | 7/1997 | Zeng et al. | |
| 5,656,498 A | 8/1997 | Iijima et al. | |
| 5,662,644 A | 9/1997 | Swor | |
| 5,664,574 A | 9/1997 | Chance | |
| 5,673,701 A | 10/1997 | Chance | |
| 5,689,241 A | 11/1997 | Clarke, Sr. et al. | |
| 5,699,798 A | 12/1997 | Hochman et al. | |
| 5,707,986 A | 1/1998 | Miller et al. | |
| 5,732,707 A | 3/1998 | Widder et al. | |
| 5,743,266 A | 4/1998 | Levene et al. | |
| 5,756,541 A | 5/1998 | Strong et al. | |
| 5,785,965 A | 7/1998 | Pratt et al. | |
| 5,803,914 A | 9/1998 | Ryals et al. | |
| 5,827,190 A | 10/1998 | Palcic et al. | |
| 5,845,639 A | 12/1998 | Hochman et al. | |
| 5,851,181 A | 12/1998 | Talmor | |
| 5,865,754 A | 2/1999 | Sevick-Muraca et al. | |
| 5,910,510 A | 6/1999 | Strong et al. | |
| 5,919,616 A | 7/1999 | Aurelian et al. | |
| 5,927,284 A | 7/1999 | Borst et al. | |
| 5,935,942 A | 8/1999 | Zeimer | |
| 5,951,980 A | 9/1999 | Collen | |
| 5,956,435 A | 9/1999 | Buzug et al. | |
| 5,965,356 A | 10/1999 | Aurelian et al. | |
| 5,999,841 A | 12/1999 | Aoyagi et al. | |
| 6,008,889 A | 12/1999 | Zeng et al. | |
| 6,013,265 A | 1/2000 | Aurelian | |
| 6,021,344 A | 2/2000 | Lui et al. | |
| 6,032,070 A | 2/2000 | Flock et al. | |
| 6,054,131 A | 4/2000 | Aurelian | |
| 6,069,689 A | 5/2000 | Zeng et al. | |
| 6,074,627 A | 6/2000 | Dean et al. | |
| 6,081,612 A | 6/2000 | Gutkowicz-Krusin et al. | |
| 6,093,149 A | 7/2000 | Guracar et al. | |

(56) References Cited

U.S. PATENT DOCUMENTS

| | | |
|---|---|---|
| 6,122,042 A | 9/2000 | Wunderman et al. |
| 6,140,314 A | 10/2000 | Zeimer |
| 6,148,227 A | 11/2000 | Wagnières et al. |
| 6,149,671 A | 11/2000 | Nordquist et al. |
| 6,162,242 A | 12/2000 | Peyman |
| 6,179,421 B1 | 1/2001 | Pang |
| 6,186,628 B1 | 2/2001 | Van de Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imasizumi et al. |
| 6,319,273 B1 | 11/2001 | Cheen et al. |
| 6,331,703 B1 | 12/2001 | Yarnall et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,485,413 B1 | 11/2002 | Boppart et al. |
| 6,498,945 B1 | 12/2002 | Alfheim et al. |
| 6,544,183 B2 | 4/2003 | Leeson et al. |
| 6,566,641 B1 | 5/2003 | Suda |
| 6,603,552 B1 | 8/2003 | Cline et al. |
| 6,621,917 B1 | 9/2003 | Vilser |
| 6,631,286 B2 | 10/2003 | Pfeiffer et al. |
| 6,671,540 B1 | 12/2003 | Hochman |
| 6,757,554 B2 | 6/2004 | Rubinstein et al. |
| 6,804,549 B2 | 10/2004 | Hayashi |
| 6,821,946 B2 | 11/2004 | Goldspink et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,899,675 B2 | 5/2005 | Cline et al. |
| 6,915,154 B1 | 7/2005 | Docherty et al. |
| 6,936,043 B2 | 8/2005 | Peyman |
| 6,944,493 B2 | 9/2005 | Alam et al. |
| 7,113,817 B1 | 9/2006 | Winchester, Jr. et al. |
| 7,236,815 B2 | 6/2007 | Richards-Kortum et al. |
| 7,364,574 B2 | 4/2008 | Flower |
| 7,381,400 B2 | 6/2008 | Woltering |
| 7,400,753 B2 | 7/2008 | Seino et al. |
| 7,400,755 B2 | 7/2008 | West et al. |
| 7,482,318 B2 | 1/2009 | Aurelian et al. |
| 7,581,191 B2 | 8/2009 | Rice et al. |
| 7,881,777 B2 | 2/2011 | Docherty et al. |
| 7,885,438 B2 | 2/2011 | Uppaluri et al. |
| 8,036,437 B2 | 10/2011 | Arditi et al. |
| 8,073,224 B2 | 12/2011 | Strobel et al. |
| 8,144,958 B2 | 3/2012 | Nahm et al. |
| 8,185,176 B2 | 5/2012 | Mangat et al. |
| 8,285,353 B2 | 10/2012 | Choi et al. |
| 8,361,775 B2 | 1/2013 | Flower |
| 8,406,860 B2 | 3/2013 | Dvorsky et al. |
| 8,480,579 B2 | 7/2013 | Serov et al. |
| 8,521,260 B2 | 8/2013 | Grinvald et al. |
| 8,538,107 B2 | 9/2013 | Röttger |
| 8,647,605 B2 | 2/2014 | Mangat et al. |
| 8,892,190 B2 | 11/2014 | Docherty et al. |
| 8,929,974 B2 | 1/2015 | Hauger et al. |
| 8,965,488 B2 | 2/2015 | Dvorsky et al. |
| 9,129,366 B2 | 9/2015 | Nahm et al. |
| 9,351,644 B2 | 5/2016 | Nahm et al. |
| 9,357,931 B2 | 6/2016 | Nahm et al. |
| 9,421,280 B2 | 8/2016 | Mangat et al. |
| 2002/0025541 A1 | 2/2002 | Nelson et al. |
| 2002/0038120 A1 | 3/2002 | Duhaylongsod et al. |
| 2002/0099279 A1 | 7/2002 | Pfeiffer et al. |
| 2002/0099295 A1 | 7/2002 | Gil et al. |
| 2002/0146369 A1 | 10/2002 | Goldenberg |
| 2002/0181752 A1 | 12/2002 | Wallo et al. |
| 2002/0183621 A1 | 12/2002 | Pfeiffer et al. |
| 2003/0032885 A1 | 2/2003 | Rubinstein et al. |
| 2003/0050543 A1 | 3/2003 | Hartmann |
| 2003/0060718 A1 | 3/2003 | Alam et al. |
| 2003/0060722 A1 | 3/2003 | Pfeiffer et al. |
| 2003/0064025 A1 | 4/2003 | Yang et al. |
| 2003/0093064 A1 | 5/2003 | Peyman |
| 2003/0093065 A1 | 5/2003 | Peyman |
| 2003/0156252 A1 | 8/2003 | Morris et al. |
| 2003/0187349 A1 | 10/2003 | Kaneko et al. |
| 2003/0232016 A1 | 12/2003 | Heinrich |
| 2003/0236458 A1 | 12/2003 | Hochman |
| 2004/0066961 A1 | 4/2004 | Spreeuwers et al. |
| 2004/0077952 A1 | 4/2004 | Rafter et al. |
| 2004/0109231 A1 | 6/2004 | Haisch et al. |
| 2004/0156782 A1 | 8/2004 | Alam et al. |
| 2004/0162489 A1 | 8/2004 | Richards-Kortum et al. |
| 2004/0171827 A1 | 9/2004 | Peng et al. |
| 2004/0174495 A1 | 9/2004 | Levine |
| 2005/0019744 A1 | 1/2005 | Bertuglia |
| 2005/0020891 A1 | 1/2005 | Rubinstein et al. |
| 2005/0033145 A1 | 2/2005 | Graham et al. |
| 2005/0069525 A1 | 3/2005 | Mikael |
| 2005/0089866 A1 | 4/2005 | Hinuma et al. |
| 2005/0107380 A1 | 5/2005 | Nimmo et al. |
| 2005/0182321 A1 | 8/2005 | Frangioni |
| 2005/0182327 A1 | 8/2005 | Petty et al. |
| 2005/0182431 A1 | 8/2005 | Hausen et al. |
| 2005/0182434 A1 | 8/2005 | Docherty et al. |
| 2005/0187477 A1 | 8/2005 | Serov et al. |
| 2005/0197583 A1 | 9/2005 | Chance |
| 2005/0254008 A1 | 11/2005 | Ferguson et al. |
| 2006/0013768 A1 | 1/2006 | Woltering |
| 2006/0079750 A1 | 4/2006 | Fauci et al. |
| 2006/0108509 A1 | 5/2006 | Frangioni et al. |
| 2006/0147897 A1 | 7/2006 | Grinvald et al. |
| 2006/0239921 A1 | 10/2006 | Mangat et al. |
| 2006/0241499 A1 | 10/2006 | Irion et al. |
| 2007/0122344 A1 | 5/2007 | Golijanin |
| 2007/0122345 A1 | 5/2007 | Golijanin |
| 2007/0203413 A1 | 8/2007 | Frangioni |
| 2007/0254276 A1 | 11/2007 | Deutsch et al. |
| 2008/0007733 A1 | 1/2008 | Marks et al. |
| 2008/0015446 A1 | 1/2008 | Mahmood et al. |
| 2008/0071176 A1 | 3/2008 | Docherty et al. |
| 2008/0161744 A1 | 7/2008 | Golijanin et al. |
| 2008/0221421 A1 | 9/2008 | Choi et al. |
| 2008/0221648 A1 | 9/2008 | Flower |
| 2008/0239070 A1 | 10/2008 | Westwick et al. |
| 2008/0319309 A1 | 12/2008 | Bredno et al. |
| 2009/0005693 A1 | 1/2009 | Brauner et al. |
| 2009/0048516 A1 | 2/2009 | Yoshikawa et al. |
| 2009/0054788 A1 | 2/2009 | Hauger et al. |
| 2009/0118623 A1 | 5/2009 | Serov et al. |
| 2009/0137902 A1 | 5/2009 | Frangioni et al. |
| 2009/0297004 A1 | 12/2009 | Baumgart |
| 2010/0022898 A1 | 1/2010 | Rubinstein et al. |
| 2010/0036217 A1 | 2/2010 | Choi et al. |
| 2010/0061604 A1 | 3/2010 | Nahm et al. |
| 2010/0222673 A1 | 9/2010 | Mangat et al. |
| 2010/0286529 A1 | 11/2010 | Carroll et al. |
| 2011/0013002 A1 | 1/2011 | Thompson et al. |
| 2011/0063427 A1 | 3/2011 | Fengler et al. |
| 2011/0098685 A1 | 4/2011 | Flower |
| 2011/0306877 A1 | 12/2011 | Dvorsky et al. |
| 2012/0078093 A1 | 3/2012 | Flower |
| 2012/0165662 A1 | 6/2012 | Nahm et al. |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0345560 A1 | 12/2013 | Ferguson, Jr. et al. |
| 2014/0308656 A1 | 10/2014 | Flower |
| 2014/0316262 A1 | 10/2014 | Havens |

(56) References Cited

U.S. PATENT DOCUMENTS

| | | |
|---|---|---|
| 2015/0112192 A1 | 4/2015 | Docherty et al. |
| 2015/0112193 A1 | 4/2015 | Docherty et al. |
| 2015/0230710 A1 | 8/2015 | Nahm et al. |
| 2015/0230715 A1 | 8/2015 | Nahm et al. |
| 2016/0038027 A1 | 2/2016 | Brzozowski et al. |
| 2016/0110870 A1 | 4/2016 | Moriyama et al. |

FOREIGN PATENT DOCUMENTS

| | | |
|---|---|---|
| CA | 2413033 A1 | 3/2000 |
| CN | 1049781 A | 3/1991 |
| CN | 1200174 A | 11/1998 |
| CN | 1399528 A | 2/2003 |
| DE | 39 06 860 A1 | 9/1989 |
| DE | 19608027 A1 | 9/1996 |
| DE | 101 20 980 A1 | 11/2002 |
| DE | 69727220 T2 | 12/2004 |
| EP | 0091805 A2 | 10/1983 |
| EP | 0215772 A2 | 3/1987 |
| EP | 0512965 A1 | 11/1992 |
| EP | 0792618 A1 | 9/1997 |
| EP | 0826335 A1 | 3/1998 |
| EP | 1 761 171 A2 | 3/2007 |
| EP | 1874181 A1 | 1/2008 |
| GB | 2203831 A | 10/1988 |
| JP | S58-222331 A | 12/1983 |
| JP | S59-069721 A | 4/1984 |
| JP | S59-070903 A | 4/1984 |
| JP | 02-200237 A | 8/1990 |
| JP | H03-115958 A | 5/1991 |
| JP | 04-297236 A | 10/1992 |
| JP | H05-264232 A | 10/1993 |
| JP | H06-007353 A | 1/1994 |
| JP | 06-335451 A | 12/1994 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222723 A | 8/1995 |
| JP | H07-250804 A | 10/1995 |
| JP | H07-250812 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | A-H09-308609 | 12/1997 |
| JP | H09-309845 A | 12/1997 |
| JP | H10-503480 A | 3/1998 |
| JP | H10-085222 A | 4/1998 |
| JP | H10-104070 A | 4/1998 |
| JP | H10-151104 A | 6/1998 |
| JP | H10-506440 A | 6/1998 |
| JP | H10-506550 A | 6/1998 |
| JP | H10-201700 A | 8/1998 |
| JP | H10-201707 A | 8/1998 |
| JP | H11-137517 A | 5/1999 |
| JP | H11-155812 A | 6/1999 |
| JP | H11-509748 A | 8/1999 |
| JP | 2002-219129 A | 8/2002 |
| JP | A-2003-510121 | 3/2003 |
| JP | 2003-144401 A | 5/2003 |
| JP | A-2004-528917 | 9/2004 |
| JP | 2006-503620 A | 2/2006 |
| JP | A-2006-192280 | 7/2006 |
| JP | A-2007-21006 | 2/2007 |
| JP | 3896176 B2 | 3/2007 |
| JP | A-2008-525126 | 7/2008 |
| JP | 2008-535600 A | 9/2008 |
| JP | A-2008-231113 | 10/2008 |
| JP | 2010-505582 A | 2/2010 |
| JP | 2011-509768 A | 3/2011 |
| JP | 59-18532 B2 | 5/2016 |
| KR | 90-0005434 B1 | 7/1990 |
| KR | 2002-0064287 A | 8/2002 |
| RU | 2288633 C1 | 12/2006 |
| WO | WO-86/02730 A1 | 5/1986 |
| WO | WO-90/10219 A1 | 9/1990 |
| WO | WO-90/12536 A1 | 11/1990 |
| WO | WO-93/25141 A1 | 12/1993 |
| WO | WO-94/12092 A1 | 6/1994 |
| WO | WO-95/00171 A1 | 1/1995 |
| WO | WO-95/26673 A2 | 10/1995 |
| WO | WO-96/09435 A1 | 3/1996 |
| WO | WO-96/09792 A1 | 4/1996 |
| WO | WO-96/18415 A1 | 6/1996 |
| WO | WO-96/23524 A1 | 8/1996 |
| WO | WO-96/39925 A1 | 12/1996 |
| WO | WO-97/08538 A1 | 3/1997 |
| WO | WO-98/24360 A1 | 6/1998 |
| WO | WO-98/30144 A1 | 7/1998 |
| WO | WO-98/46122 A1 | 10/1998 |
| WO | WO-99/00053 A1 | 1/1999 |
| WO | WO-99/47940 A1 | 9/1999 |
| WO | WO-99/53832 A1 | 10/1999 |
| WO | WO-00/42910 A1 | 7/2000 |
| WO | WO-00/47107 A1 | 8/2000 |
| WO | WO 01/08552 A1 | 2/2001 |
| WO | WO-01/17561 A1 | 3/2001 |
| WO | WO-01/22870 A1 | 4/2001 |
| WO | WO 01/22870 A1 | 4/2001 |
| WO | WO-01/39764 A2 | 6/2001 |
| WO | WO-01/69244 A2 | 9/2001 |
| WO | WO 01/80734 A1 | 11/2001 |
| WO | WO 01/82786 A2 | 11/2001 |
| WO | WO-02/061390 A2 | 8/2002 |
| WO | WO-03/006658 A1 | 1/2003 |
| WO | WO-2004/006963 A1 | 1/2004 |
| WO | WO 2004/052195 A1 | 6/2004 |
| WO | WO-2005/026319 A2 | 3/2005 |
| WO | WO-2005/034747 A1 | 4/2005 |
| WO | WO 2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO 2006/123742 A1 | 11/2006 |
| WO | WO-2007/028032 A2 | 3/2007 |
| WO | WO-2008/044822 A1 | 4/2008 |
| WO | WO-2008/070269 A2 | 6/2008 |
| WO | WO-2008/070269 A3 | 6/2008 |
| WO | WO-2009/046985 A2 | 4/2009 |
| WO | WO-2009/046985 A3 | 4/2009 |
| WO | WO 2009/048660 A2 | 4/2009 |
| WO | WO 2009/092162 A1 | 7/2009 |
| WO | WO 2009/127972 A2 | 10/2009 |
| WO | WO-2012/038824 A1 | 3/2012 |
| WO | WO-2012/096878 A2 | 7/2012 |

OTHER PUBLICATIONS

Detter, C. et al. "Fluorescent Cardiac Imaging: A Novel Intraoperative Method for Quantitative Assessment of Myocardial Perfusion During Graded Coronary Artery Stenosis." Circulation, Aug. 1, 2007, pp. 1007-1014, vol. 116, No. 9.

Detter, C. et al. "Near-Infrared Fluorescence Coronary Angiography: A New Noninvasive Technology for Intraoperative Graft Patency Control." The Heart Surgery Forum, Jun. 2011, pp. 364-369, vol. 5, Issue 4.

Forrester et al. "Comparison of Laser Speckle and Laser Doppler Perfusion Imaging: Measurement in Human Skin and Rabbit Articular Tissue." Medical and Biological Engineering and Computing, Nov. 1, 2002, pp. 687-697, vol. 40, No. 6.

(56) References Cited

OTHER PUBLICATIONS

Frenzel H. et al. "In vivo perfusion analysis of normal and dysplastic ears and its implication on total auricular reconstruction." Journal of Plastic, Reconstructive and Aesthetic Surgery, Apr. 18, 2008, pp. S21-S28, vol. 61.
Holm, et al. "Intraoperative evaluation of skin-flap viability using laser-induced fluorescence of indocyanine green." British Journal of Plastice Surgery, Dec. 1, 2002, pp. 635-644, vol. 55, No. 8.
Holm et al. "Laser-Induced Fluorescence of Indocyanine Green: Plastic Surgical Applications." European Journal of Plastic Surgery, Feb. 25, 2003, pp. 19-25, vol. 26.
Holm et al. "Monitoring Free Flaps Using Laser-Indeuced Fluorescence of Indocyanine Green: A Preliminary Experience." Wiley Interscience, 2002, pp. 278-287.
Jolion, J. et al. "Robust Clustering with Applications in Computer Vision." IEEE Transactions on Pattern Analysis and Machine Intelligence, Aug. 1991, pp. 791-802, vol. 13, No. 8.
Krishnan K. G. et al. "The role of near-infrared angiography in the assessment of postoperative veneous congestion in random pattern, pedicled island and free flaps." British Journal of Plastic Surgery, Apr. 1, 2005, pp. 330-338, vol. 58, No. 3.
Martinez-Perez, M. et al. "Unsupervised Segmentation Based on Robust Estimation and Cooccurrence Data." Proceedings of the International Conference on Miage Processing (ICIP) Lausanne, Sep. 19, 1996, pp. 943-945, vol. 3.
"Novadaq Imaging System Receives FDA Clearance for use During Plastic Reconstructive Surgery." PR Newswire, Jan. 29, 2007, 3 pages.
Newman et al. "Update on the Application of Laser-Assisted Indocyanine Green Fluorescent Dye Angiography in Microsurgical Breast Reconstruction." Oct. 31, 2009, 2 pages.
Pandharipande et al. "Perfusion Imaging of the Liver: Current Challenges and Future Goals." Radiology, 2005, pp. 661-673.
Sezgin, M. et al. "Survey over image thresholding techniques and quantitative performance evaluation." Journal of Electronic Imaging, Jan. 2004, pp. 146-165, vol. 13(1).
Verbeek, X. "High-Resolution Functional Imaging With Ultrasound Contrast Agents Based on RF Processing in an Un Vivo Kidney Experiment." Ultrasound in Med. & Biol., 2001, pp. 223-233, vol. 27, No. 2.
Yamaguchi et al. "Evaluation of Skin Perfusion After Nipple-Sparing Mastectomy by Indocyanine Green Dye." (With English Abstract) Journal of Saitama Medical University, Japan, Apr. 2005, pp. 45-50, vol. 32, No. 2.
Jan. 25, 2012 International Search Report issued in Application No. PCT/IB11/002381.
Jul. 3, 2012 Translation of Chinese Office Action issued in Chinese Application No. 200980123414.0.
Mar. 29, 2013 Translation of Russian Office Action issued in Russian Application No. 2011111078/14.
May 23, 2013 Translation of Chinese Office Action issued in Chinese Application No. 200980123414.0.
May 30, 2013 Mexican Office Action issued in Mexican Application No. MX/a/2010/011249.
Jul. 29, 2013 Translation of Russian Decision on Grant issued in Russian Application No. 2011111078/14.
Jul. 30, 2013 Translation of Japanese Office Action dated Jul. 30, 2013 issued in Japanese Application No. 2011-504574.
May 15, 2014 Supplemental European Search Report and Written Opinion issued in European Application No. 09 732 993.2.
Chinese Office Action mailed on Nov. 12, 2015, for Chinese Patent Application No. 201180057244.8, filed on Sep. 20, 2010, five pages.
European Office Action mailed on Mar. 27, 2015, for EP Application No. 09 732 993.2, filed on Apr. 14, 2008, six pages.
Extended European Search Report mailed on Feb. 22, 2012, for EP Application No. 09 704 642.9, filed on Jan. 25, 2008, fifteen pages.
Extended European Search Report mailed on Apr. 28, 2014, for EP Application No. 09 732 993.2, filed on Apr. 14, 2008, eight pages.
Extended European Search Report mailed on Jan. 28, 2014, for EP Application No. 11 826 475.3, filed on Sep. 20, 2010, six pages.
Final Office Action mailed on May 29, 2013, for U.S. Appl. No. 12/933,477, filed Sep. 20, 2010, twelve pages.
Final Office Action mailed on Jun. 25, 2014, for U.S. Appl. No. 12/933,477, filed Sep. 20, 2010, fifteen pages.
Final Office Action mailed on Sep. 17, 2015, for U.S. Appl. No. 12/933,477, filed Sep. 20, 2010, six pages.
International Search Report mailed on Jun. 8, 2009, for PCT Patent Application No. PCT/CA2009/000073, filed on Jan. 23, 2009, three pages.
International Search Report mailed on Dec. 3, 2009, for PCT Patent Application No. PCT/IB2009/005700, filed on Apr. 14, 2009, three pages.
Japanese Office Action mailed on Sep. 14, 2015, for Japanese Patent Application No. 2011-504574, filed on Apr. 14, 2009, five pages.
Korean Office Action mailed on Nov. 30, 2015, for Korean Patent Application No. 10-2010-7024977, filed on Apr. 14, 2009, two pages.
Non-Final Office Action mailed on Sep. 5, 2012, for U.S. Appl. No. 12/933,477, filed Sep. 20, 2010, seven pages.
Non-Final Office Action mailed on Dec. 20, 2013, for U.S. Appl. No. 12/933,477, filed Sep. 20, 2010, thirteen pages.
Non-Final Office Action mailed on Apr. 1, 2015, for U.S. Appl. No. 12/933,477, filed Sep. 20, 2010, fourteen pages.
Notice of Allowance mailed on Oct. 18, 2012, for U.S. Appl. No. 12/841,659, filed Jul. 22, 2010, seven pages.
Notice of Allowance mailed on Aug. 7, 2014, for U.S. Appl. No. 13/850,063, filed Mar. 25, 2013, nine pages.
Notice of Allowance mailed on Oct. 16, 2014, for U.S. Appl. No. 13/850,063, filed Mar. 25, 2013, eight pages.
Notice of Allowance mailed on Oct. 29, 2015, for EP Application No. 09 704 642.9, filed on Jan. 25, 2008, two pages.
Notice of Allowance mailed on Oct. 21, 2015, for EP Application No. 11 826 475.3, filed on Sep. 20, 2010, eight pages.
Written Opinion of the International Searching Authority mailed on Jun. 8, 2009, for PCT Patent Application No. PCT/CA2009/000073, filed on Jan. 23, 2009, four pages.
Written Opinion of the International Searching Authority mailed on Dec. 3, 2009, for PCT Patent Application No. PCT/IB2009/005700, filed on Apr. 14, 2009, six pages.
Written Opinion of the International Searching Authority mailed on Feb. 1, 2012, for PCT Patent Application No. PCT/IB2011/002381, filed on Sep. 20, 2011, four pages.
Canadian Office Action dated Sep. 30, 2015, for CA Application No. 2,811,847, filed on Sep. 20, 2011, four pages.
Canadian Office Action dated Mar. 16, 2016, for CA Application No. 2,750,760 filed on Jan. 23, 2009, five pages.
Japanese Office Action mailed on Mar. 29, 2016, for Japanese Patent Application No. 2013-529729, filed on Mar. 21, 2013, and an English translation of the same, seven pages.
Korean Notice of Allowance mailed on Apr. 29, 2016, for Korean Patent Application No. 10-2010-7024977, filed on Apr. 14, 2009, and an English translation of the same, three pages.
Summons to attend Oral Proceedings pursuant to Rule 115(1) EPC issued on Apr. 25, 2016, for European patent application No. 09732993.2, filed on Apr. 14, 2009, five pages.
Japanese Notice of Allowance mailed Sep. 16, 2016, for Japanese Patent Application No. 2015-517876 filed on Jun. 20, 2013, six pages.
Akintunde, A. et al. (Oct.-Nov. 1992). "Quadruple Labeling of Brain-Stem Neurons: A Multiple Retrograde Fluorescent Tracer Study of Axonal Collateralization," *Journal of Neuroscience* Methods 45(1-2):15-22.
Alander, J.T. et al. (Jan. 1, 2012). "A Review of Indocyanine Green Fluorescent Imaging in Surgery," *International Journal of Biomedical Imaging* 2012:1-26, article ID 940585.
Alfano et al. (Oct. 1987). "Fluorescence Spectra from Cancerous and Normal Human Breast and Lung Tissues," *IEEE Journal of Quantum Electronics* QE-23(10):1806-1811.
Alm, A. et al. (Jan. 1, 1973). "Ocular and Optic Nerve Blood Flow at Normal and Increased Intraocular Pressures in Monkeys (Macaca irus): A Study with Radioactively Labelled Microspheres Including

(56) References Cited

OTHER PUBLICATIONS

Flow Determinations in Brain and Some Other Tissues," *Experimental Eye Research* 15(1):15-29.

Alonso-Burgos, A. et al. (2006). "Preoperative planning of deep inferior epigastric artery perforator flap reconstruction with multi-slice-CT angiography: imaging findings and initial experience," *Journal of Plastic, Reconstructive & Aesthetic Surgery* 59:585-593.

Alvarez, F. J. et al. (Apr. 1996). "Behaviour of Isolated Rat and Human Red Blood Cells Upon Hypotonic-Dialysis Encapsulation of Carbonic Anhydrase And Dextran," *Biotechnology and Applied Biochemistry* 23(2):173-179.

Ancalmo, N. et al. (1997). "Minimally invasive coronary artery bypass surgery: really minimal?" *Ann. Thorac. Surg.* 64:928-929.

Andersson-Engels, S. et al. (1991). "Fluorescence Characteristics of Atherosclorotic Plaque and Malignant Tumors," in *Optical Methods for Tumor Treatment and Early Diagnosis: Mechanisms and Techniques*, T. J. Dougherty (Ed.), The Society of Photo-optical Instrumentation Engineers (SPIE) 1426:31-43, fourteen pages.

Andersson-Engels, S. et al. (Mar. 1989). "Tissue Diagnostics Using Laser-Induced Fluorescence," *Berichte der Bunsengesellschaft für physikalische Chemie* 93(3):335-342.

Angelov, D.N. et al. (Apr. 1999). "Contralateral Trigeminal Nerve Lesion Reduces Polyneuronal Muscle Innervation after Facial Nerve Repair in Rats," *European Journal of Neuroscience* 11(4):1369-1378.

Annese, V. et al. (2005). "Erthrocytes-Mediated Delivery of Dexamethasone in Steroid-Dependent IBD Patients—a Pilot Uncontrolled Study," *American Journal of Gastroenterology* 100:1370-1375.

Argus-50/CA, Inter cellular CA2+ (calcium ion) Image Analysis system, Observation and 2-dimensional analysis of Ca2+ concentration distribution. Fura-2 and Indo-1 compatible. Ca2+ concentrations are calculated from the fluorescence ratio, Feb. 1992, pp. 1-10.

Author Unknown, "Invitrogen," Material Safety Data Sheet, Jun. 4, 2008, p. 1-4.

Awano, T. et al. (Jun. 2010). "Intraoperative EC-IC Bypass Blood Flow Assessment with Indocyanine Green Angiography in Moyamoya and Non-moyamoya Ischemic Stroke," *World Neurosurg.* 73(6):668-674.

Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.

Barton, J.K. et al. (1999) "Simultaneous irradiation and imaging of blood vessels during pulsed laser delivery," *Lasers in Surgery and Medicine* 24(3):236-243.

Bassingthwaighte, J.B. et al. (Apr. 1974). "Organ Blood Flow, Wash-in, Washout, and Clearance of Nutrients and Metabolites," *Mayo Clin. Proc.* 49(4):248-255.

Batliwala, H. et al. (Apr. 15, 1995). "Methane-Induced Haemolysis of Human Erythrocytes," *Biochemical J.* 307(2):433-438.

Bek, T. (1999). "Diabetic Maculopathy Caused by Disturbances in Retinal Vasomotion: A New Hypothesis," *Acta Ophthalmologica Scandinavica* 77:376-380.

Benson, R.C. et al. (1978). "Fluorescence Properties of Indocyanine Green as Related to Angiography," *Phys. Med. Biol.* 23(1):159-163.

Black's Medical Dictionary, "Perfusion," 42nd Edition (2009), two pages.

Boer, F. et al. (1994). "Effect of Ventilation on First-Pass Pulmonary Retention of Alfentaril and Sufentanil in Patients Undergoing Coronary Artery Surgery," *British Journal Anesthesia* 73:458-463.

Boldt, J. et al. (Feb. 1990). "Lung management during cardiopulmonary bypass: influence on extravascular lung water," *Journal of Cardiothoracic Anesthesia* 4(1):73-79.

Boldt, J. et al. (1991). "Does the technique of cardiopulmonary bypass affect lung water content?" *European Journal of Cardio-Thoracic Surgery* 5:22-26.

Bütter, A. et al. (May 2005). "Melanoma in Children and the Use of Sentinel Lymph Node Biopsy," *Journal of Pediatric Surgery* 40(5):797-800.

C2741, Compact High Performance video camera for industrial applications with Built-in contrast enhancement circuit, Jun. 1998.

Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.

Coffey, J.H. et al. (1984). "Evaluation of Visual Acuity During Laser Photoradiation Therapy of Cancer," *Lasers in Surgery and Medicine* 4(1):65-71.

Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.

Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.

Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.

Dail, W.G. et al. (Oct. 1999). "Multiple Vasodilator Pathways from the Pelvic Plexus to the Penis of the Rat," *International Journal of Impotence Research* 11(5):277-285.

Dan, A.G. et al. (Nov. 2004). "1% Lymphazurin vs 10% Fluorescein for Sentinel Node Mapping in Colorectal Tumors," *Arch Surg.* 139(11):1180-1184.

Daniels, G. et al. (Apr. 2007). "Towards Universal Red Blood Cell," *Nature Biotechnology* 25(4):427-428.

De Flora, A. (Sep. 1986). "Encapsulation of Adriamycin in human erythrocytes," *Proc. Natl. Acad. Sci., USA* 83(18):7029-7033.

De-Grand, A.M. et al. (Dec. 2003). "An Operational Near Infrared Fluorescence Imaging System Prototype for Large Animal Surgery," *Technology in Cancer Research & Treatment* 2(6):1-10.

Deloach, J.R. (ed.) et al. (1985). *Red Blood Cells as Carriers for Drugs. A Method for Disseminating Chemotherapeutics, Hormones, Enzymes and Other Therapeutic Agents via the Circulatory System*, Karger, Basel, CH, pp. v-vii, (Table of Contents).

Deloach, J.R. (Jun. 1983). "Encapsulation of Exogenous Agents in Erythrocytes and the Circulating Survival of Carrier Erythrocytes," *Journal of Applied Biochemistry* 5(3):149-157.

Demos (May/Jun. 2004). "Near-Infrared Autofluorescence Imaging for Detection of Cancer," *Journal of Biomedical Optics* 9(3):587-592.

Desai, N.D. et al. (Oct. 18, 2005, e-published on Sep. 28, 2005) "Improving the Quality of Coronary Bypass Surgery with Untraoperative Angiography," *Journal of the American College of Cardiology* 46(8):1521-1525.

Dietz, F.B. et al. (Feb. 2003). "Indocyanine Green: Evidence of Neurotoxicity in Spinal Root Axons," *Anesthesiology* 98(2):516-520.

Digital CCD Microscopy (date unknown). Chapter 14, pp. 259-282,.

Dougherty, T.J. et al. (1990). "Cutaneous Phototoxic Occurrences in Patients Receiving Photofrin," *Lasers in Surgery and Medicine* 10(5):485-488.

Draijer, M.J. et al. (Jun. 17-19, 2007). "Laser Doppler Perfusion Imaging with a High-Speed CMOS-Camera," in *Novel Optical Instrumentation for Biomedical Applications III*, C. Deperursinge, ed., Proceedings of SPIE-OSA Biomedical Optics (Optical Society of America, 2007), SPIE-OSA, 6631:0N1-0N7, nine pages.

Dünne, A. et al. (Nov. 2001)."Value of Sentinel lymphonodectomy in Head and Neck Cancer Patients without Evidence of Lymphogenic Metastatic Disease," *Auris Nasus Larynx* 28(4):339-344.

Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.

Emery R.W. et al. (Aug. 1996). "Revascularization Using Angioplasty and Minimally Invasive Techniques Documented by Thermal Imaging," *The Annals of Thoracic Surgery* 62(2):591-593.

(56) References Cited

OTHER PUBLICATIONS

Eren, S. et al. (Dec. 1995). "Assessment of Microcirculation of an Axial Skin Flap Using Indocyanine Green Fluorescence Angiography," *Plast. Reconstr. Surg.* 96(7):1636-1649.

Flower, R. et al. (Apr.-Jun. 1999). "Effects of Free and Liposome-Encapsulated Hemoglobin on Choroidal Vascular Plexus Blood Flow, Using the Rabbit Eye as a Model System," *European Journal of Ophthalmology* 9(2):103-114.

Flower, R.W. (1992). "Choroidal Angiography Today and Tomorrow," *Retina* 12(3):189-190.

Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.

Flower, R.W. (Aug. 2002). "Optimizing Treatment of Choroidal Neovascularization Feeder Vessels Associated with Age-Related Macular Degeneration," *American Journal of Ophthalmology* 134(2):228-239.

Flower, R.W. (Dec. 1973). "Injection Technique for Indocyanine Green and Sodium Fluorescein Dye Angiography of the Eye," *Investigative Opthamology* 12(12):881-895.

Flower, R.W. (Sep. 1, 1994). "Does Preinjection Binding of Indocyanine Green to Serum Actually Improve Angiograms?," *Arch Ophthalmol.* 112(9):1137-1139.

Flower, R.W. et al. (Aug. 1977). "Quantification of Indicator Dye Concentration in Ocular Blood Vessels," *Exp. Eye Res.* 25(2):103-111.

Flower, R.W. et al. (Dec. 1, 2008, e-published Aug. 15, 2008). "Observation of Erythrocyte Dynamics in the Retinal Capillaries and Choriocapillaris Using ICG-Loaded Erythrocyte Ghost Cells," Investigative Ophthalmology, & Visual Science 49(12):5510-5516.

Flower, R.W. et al. (Mar. 26, 2008-Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).

Frangioni, J.V. (Oct. 2003). "In Vivo Near-Infrared Fluorescence Imaging," *Current Opinion in Chemical Biology* 7(5):626-634.

Fritzsch, B. et al. (Aug. 1991). "Sequential Double Labeling With Different Fluorescent Dyes Coupled to Dextran Amines as a Tool to Estimate the Accuracy of Tracer Application and of Regeneration," *Journal of Neuroscience Methods* 39(1):9-17.

Gagnon, A.R. et al. (2006). "Deep and superficial inferior epigastric artery perforator flaps," *Cirugia Plástica Ibero-Latinoamericana* 32(4):7-13.

Gardner, T.J. (1993). "Coronary artery disease and Ventricular Aneurysms," in *Surgery, Scientific Principles and Practice*, Greenfield, L.J. (ed.) et al., J.B. Lippincott Co., Philadelphia, PA, pp. 1391-1411, twenty three pages.

Garrett, W.T. et al. (Jul. 8, 1991). "Fluoro-Gold's Toxicity makes it Inferior to True Blue for Long-Term Studies of Dorsal Root Ganglion Neurons and Motoneurons," *Neuroscience Letters* 128(1):137-139.

Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal Of Physical Chemistry A* 107(18):3443-3449.

Gipponi, M. et al. (Mar. 1, 2004). "New Fields of Application of the Sentinel Lymph Node Biopsy in the Pathologic Staging of Solid Neoplasms: Review of Literature and Surgical Perspectives," *Journal of Surgical Oncology* 85(3):171-179.

Giunta, R.E. et al. (Jul. 2005). "Prediction of Flap Necrosis with Laser Induced Indocyanine Green Fluorescence in a Rat Model," *British Journal of Plastic Surgery* 58(5):695-701.

Giunta, R.E. et al. (Jun. 2000). "The Value of Preoperative Doppler Sonography for Planning Free Perforator Flaps," *Plastic and Reconstructive Surgery* 105(7):2381-2386.

Glossary, Nature, downloaded from the internet <http://www.nature.com/nrg/journal/v4/nl0/glossary/nrgl 183_glossary.html>> HTML on Jun. 30, 2014.

Glover, J.C. et al. (Nov. 1986). "Fluorescent Dextran-Amines Used as Axonal Tracers in the Nervous System of the Chicken Embryo," *Journal of Neuroscience Methods* 18(3):243-254.

Goldstein, J.A. et al. (Dec. 1998). "Intraoperative Angiography to Assess Graft Patency After Minimally Invasive Coronary Bypass," *Ann. Thorac. Surg.* 66(6):1978-1982.

Gothoskar A.V. (Mar. 2004). "Resealed Erythrocytes: A Review," *Pharmaceutical Technology* pp. 140, 142, 144, 146, 148, 150, 152 and 154-158, twelve pages.

Granzow, J.W. et al. (Jul. 2007)."Breast Reconstruction with Perforator Flaps" *Plastic and Reconstructive Surgery* 120(1):1-12.

Green, H.A. et al. (Jan. 1992). "Burn Depth Estimation Using Indocyanine Green Fluorescence," *Arch Dermatol* 128(1):43-49.

Haglund, M. et al. (Feb. 1996). "Enhanced Optical Imaging of Human Gliomas and Tumor Margins," Neurosurgery 38(2):308-317.

Haglund, M.M. et al. (Nov. 1994). "Enhanced Optical Imaging of Rat Gliomas and Tumor Margins," *Neurosurgery* 35(5):930-941.

Hallock, G.G. (Jul. 2003). "Doppler sonography and color duplex imaging for planning a perforator flap," *Clinics in Plastic Surgery* 30(3):347-357.

Hamamatsu Brochure. (May 1997). Specifications for Real-time Microscope Image Processing System: ARGUS-20 with C2400-75i.

Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.

Hayata, Y. et al. (Jul. 1982). "Fiberoptic Bronchoscopic Laser Photoradiation for Tumor Localization in Lung Cancer," *Chest* 82(1):10-14.

He, Z. (Feb. 2009). "Fluorogold Induces Persistent Neurological Deficits and Circling Behavior in Mice Over-Expressing Human Mutant Tau," *Current Neurovascular Research* 6(1):54-61.

Herts, B.R. (May 2003). "Imaging for Renal Tumors," *Current Opin. Urol.* 13(3):181-186.

Hirano et al. (1989). "Photodynamic Cancer Diagnosis and Treatment System Consisting of Pulse Lasers and an Endoscopic Spectro-Image Analyzer," Laser in Life Sciences 3(2):99-116.

Humblet, V. et al. (Oct. 2005). "High-Affinity Near-Infrared Fluorescent Small-Molecule Contrast Agents for In Vivo Imaging of Prostate-Specific Membrane Antigen," *Molecular Imaging* 4(4):448-462.

Hung, J. et al. (1991). "Autofluorescence of Normal and Malignant Bronchial Tissue," *Lasers in Surgery and Medicine* 11(2):99-105.

Ikeda, S. (Jul. 1989). "Bronichial Telivision Endoscopy," *Chest* 96(1):41S-42S.

Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.

Jagoe, J.R. et al. (1989). "Quantification of retinal damage during cardiopulmonary bypass," Third International Conference on Image Processing and its Applications (Conf. Publ. No. 307), IEE, 1989, pp. 319-323.

Jamis-Dow, C.A. et al. (Mar. 1996). "Small (< or = 3-cm) Renal Masses: Detection with CT versus us and Pathologic Correlation," Radiology 198(3):785-788.

Kamolz, L.-P. et al. (Dec. 2003). "Indocyanine Green Video Angiographies Help to Identify Burns Requiring Operation," *Burns* 29(8):785-791.

Kapadia, C.R. et al. (Jul. 1990). "Laser-Induced Fluorescence Spectroscopy of Human Colonic Mucosa. Detection of Adenomatous Transformation," *Gastroenterology* 99(1):150-157.

Kato, H. et al. (Jun. 1985). "Early Detection of Lung Cancer by Means of Hematoporphyrin Derivative Fluorescence and Laser Photoradiation," *Clinics in Chest Medicine* 6(2):237-253.

Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.

Keon, W.J. et al. (Dec. 1979). "Coronary Endarterectomy: An Adjunct to Coronary Artery Bypass Grafting," *Surgery* 86(6):859-867.

(56) References Cited

OTHER PUBLICATIONS

Kim, S. et al. (2004, e-published Dec. 7, 2003). "Near-Infrared Fluorescent Type II Quantum Dots for Sentinel Lymph Node Mapping," *Nature Biotechnology* 22(1):93-97.

Kim, S.G. et al. (Jun. 15, 1988). "Quantitative Determination of Tumor Blood Flow and Perfusion Via Deuterium Nuclear Magnetic Resonance Spectroscopy in Mice," *Cancer Res.* 48(12):3449-3453.

Kiryu, J. et al. (Sep. 1994). "Noninvasive Visualization of the Choriocapillaris and its Dynamic Filling," *Investigative Ophthalmology & Visual Science* 35(10):3724-3731.

Kitai, T. et al. (Jul. 2005). "Fluorescence Navigation with Indocyanine Green for Detecting Sentinel Lymph Nodes in Breast Cancer," *Breast Cancer* 12(3):211-215.

Kleszcyńska, H. et al. (Mar. 2005). "Hemolysis of Erythrocytes and Erythrocyte Membrane Fluidity Changes by New Lysosomotropic Compounds," *Journal of Fluorescence* 15(2):137-141.

Köbbert, C. et al. (Nov. 2000). "Current Concepts in Neuroanatomical Tracing," *Progress in Neurobiology* 62(4):327-351.

Kokaji, K. et al. (Date Unkown). "Intraoperative Quality Assessment by Using Fluorescent Imaging in Off-pump Coronary Artery Bypass Grafting," *The Department of Cardiovascular Surgery, University of Keio*, Tokyo, Japan. (Abstract only).

Kömürcü, F. et al. (Feb. 2005). "Management Strategies for Peripheral Iatrogenic Nerve Lesions," *Annals of Plastic Surgery* 54(2):135-139.

Kuipers, J.A. et al. (1999). "Recirculatory and Compartmental Pharmacokinetic Modeling of Alfentanil Pigs, the Influence of Cardiac Output," *Anesthesiology* 90(4):1146-1157.

Kupriyanov, V.V. et al. (Nov. 2004). "Mapping Regional Oxygenation and Flow in Pig Hearts In Vivo Using Near-infrared Spectroscopic Imaging," *Journal of Molecular and Cellular Cardiology* 37(5):947-957.

Kurihara, K. et al. (Jun. 1984). "Nerve Staining with Leucomethylene Blue: An Experimental Study," *Plastic and Reconstruction Surgery* 73(6):960-964.

Kyo, S. "Use of Ultrasound Cardiology during Coronary Artery Bypass Surgery," *Heart and Blood Vessel Imaging II*.

Lam, S. et al. (1991). "Mechanism of Detection of Early Lung Cancer by Ratio Fluorometry," *Lasers in Life Sciences* 4(2):67-73.

Lam, S. et al. (Feb. 1990). "Detection of Early Lung Cancer Using Low Dose Photofrin II," *Chest* 97(2):333-337.

Lam, S. et al. (Jul. 1, 1990). "Detection of Lung Cancer by Ratio Fluorometry With and Without Photofrin II," *Proc. SPIE—Optical Fibers in Medicine V* 1201:561-568.

Lam, S. et al. (Nov. 1-4, 1990). "Fluorescence Imaging of Early Lung Cancer," *Annual International Conference of the IEEE Engineering in Medicine and Biology Society* 12(3):1142-1143.

Lam, S.C. et al. (1993). "Fluorescence Detection," Chapter 20 in *Lung Cancer*, Roth, J.A. (ed.), et al., Blackwell Scientific Publications Inc., 238 Main Street, Cambridge, Massachusetts, 02142, pp. 325-338, sixteen pages.

Lanciego, J.L. et al. (Jun. 1998). "Multiple Neuroanatomical Tracing in Primates," *Brain Research Protocols* 2(4):323-332.

Lanciego, J.L. et al. (Oct. 1998). "Multiple Axonal Tracing: Simultaneous Detection of Three Tracers in the Same Section," *Histochemistry and Cell Biology* 110(5):509-515.

Laub, G.W. et al. (Nov./Dec. 1989). "Experimental Use of Fluorescein for Visualization of Coronary Arteries," *Vascular and Endovascular Surgery* 23(6):454-457.

Lee, E.T. et al. (Mar. 1997). "A New Method for Assessment of Changes in Retinal Blood Flow," *Mecial Engineering & Physics* 19(2):125-130.

Leissner, J. et al. (Jan. 2004). "Extended Radical Lymphadenectomy in Patients with Urothelial Bladder Cancer: Results of a Prospective Multicenter Study," *The Journal of Urology* 171(1):139-144.

Leithner, "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; located at http://edoc.hu-berlin.de/d issertationen/leith ner-christoph-2003-07-14/, [English Abstract and Machine Translation].

Liedberg et al. (2003). "Sentinel-Node-Diagnostik Beim Invasiven (Bladder Cancer and the Sentinel Node Concept)," *Aktuel Urol.* 34:115-118 (English Abstract Only).

Liedberg, F. et al. (Jan. 2006). "Intraoperative Sentinel Node Detection Improves Nodal Staging in Invasive Bladder Cancer," *The Journal of Urology* 175(1):84-89.

Lippincott's New Medical Dictionary. "Perfusion," p. 707 (1897), three pages.

Liptay, M.J. (Mar. 2004). "Sentinel Node Mapping in Lung Cancer," *Annals of Surgical Oncology* 11(Supplement 3):271S-274S.

Liu Q. P. et al. (Apr. 2007). "Bacterial Glycosidases for the Production of Universal Red Blood Cells" *Nature Biotechnology* 25(7):454-464.

Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.

Mack, M.J. et al. (Sep. 1998). "Arterial Graft Patency in Coronary Artery Bypass Grafting: What Do We Really Know?," *Ann. Thorac. Surg.* 66(3):1055-1059.

Magnani, M. et al. (Aug. 1998). "Erythrocyte Engineering for Drug Delivery and Targeting," *Biotechnology and Applied Biochemistry* 28(Part 1):1-6.

Magnani, M. et al. (Jul. 15, 1992). "Targeting Antiretroviral Nucleoside Analogues in Phosphorylated Form to Macrophasges: In Vitro and In Vivo Studies," *Proc. Natl. Acad. Sci. USA* 89(14):6477-6481.

Malmstrom et al. (Nov. 2002). "Early Metastatic Progression of Bladder Carcinoma: Molecular Profile of Primary Tumor and Sentinel Lymph Node," *The Journal of Urology* 168(5):2240-2244.

Malmström, P.U. et al. (Jul. 2004). "RE: Extended Radical Lymphadenectomy in Patients With Urothelial Bladder Cancer: Results of a Prospective Multicenter Study," *J. of Urol.* 172(1):386, one page.

Marangos, N. et al. (Dec. 2001). "In Vivo Visualization of the Cochlear Nerve and Nuclei with Fluorescent Axonal Tracers," *Hearing Research* 162(1-2):48-52.

May, S. (May/Jun. 1995). "Photonic Approaches to Burn Diagnostics," *Biophotonics International* pp. 44-50.

McKee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.

Merriam Webster Medline Plus Medical Dictionary. "Perfusion," located at http://www.merriam-webster.com/medlineplus/perfusion, last visited on Apr. 15, 2015, one page.

Microscope Video Camera, For Fluorescent Observation, Easy Fluorescent Image Analysis a CCD Camera.

Minciacchi, D. et al. (Jul. 1991). "A Procedure for the Simultaneous Visualization of Two Anterograde and Different Retrograde Fluorescent Tracers—Application to the Study of the Afferent-Efferent Organization of Thalamic Anterior Intralaminar Nuclei" *Journal of Neuroscience Methods* 38(2-3):183-191.

Mitaka USA, Inc. (2015). "PDE Breast Free Flap Evaluation," located at <http://mitakausa.com/category/pde_education/flaps/>, last visited on Dec. 29, 2015, four pages.

Mitaka USA, Inc. (2015). "PDE-Neo" located at <http://mitakausa.com/pde-neo/>, last visited on Dec. 29, 2015, two pages.

Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.

Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.

Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-24.

(56) References Cited

OTHER PUBLICATIONS

Motomura et al. (1999). "Sentinel Node Biopsy Guided by Indocyanine Green Dye in Breast Cancer Patients," *Japan J. Clin. Oncol.* 29(12):604-607.

Mullooly, V.M. et al. (1990). "Dihematoporphyrin Ether-Induced Photosensitivity in Laryngeal Papilloma Patients," *Lasers in Surgery and Medicine* 10(4):349-356.

Murphy (2001). "Digital CCD Microscopy," Chapter 14 in *Fundamentals of Light Microscopy and Electronic Imaging*, John Wiley and Sons, pp. i-xi and 259-281.

Nahlieli, O. et al. (Mar. 2001). "Intravital Staining with Methylene Blue as an Aid to Facial Nerve Identification in Parotid Gland Surgery" *J. Oral Maxillofac. Surgery* 59(3):355-356.

Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366.

Nakayama, A. et al. (Oct. 2002). "Functional Near-Infrared Fluorescence Imaging for Cardiac Surgery and Targeted Gene Therapy," *Molecular Imaging* 1(4):365-377.

Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," *Journal of Neuroscience Methods* 103(1):11-21.

Nimura, H. et al. (May 2004, e-published on Mar. 22, 2004). "Infrared Ray Electronic Endoscopy Combined with Indocyanine Green Injection for Detection of Sentinel Nodes of Patients with Gastric Cancer," *British Journal of Surgery* 91(5):575-579.

Oddi, A. et al. (Jun. 1996). "Intraoperative Biliary Tree Imaging with Cholyl-Lysyl-Fluorescein: An Experimental Study in the Rabbit" *Surgical Laparoscopy & Endoscopy* 6(3):198-200.

Ogata, F. et al. (Jun. 2007). "Novel Lymphography Using Indocyanine Green Dye for Near-Infrared Fluorescence Labeling," *Annals of Plastic Surgery* 58(6):652-655.

Ohnishi, S. et al. (Jul.-Sep. 2005). "Organic Alternatives to Quantum Dots for Intraoperative Near-Infrared Fluorescent Lymph Node Mapping" *Molecular Imaging* 4(3):172-181.

Ooyama, M. (Oct. 12-15, 1994). The 8th Congress of International YAG Laser Symposium, The 15th Annual Meeting of Japan Society for Laser Medicine, Sun Royal Hotel, Japan.

Ott, P. "Hepatic Elimination of Indocyanine Green with Special Reference to Distribution Kinetics and the Influence of Plasma Protein Binding," Thesis.

Oxford Concise Medical Dictionary. "Perfusion," p. 571 (1980), three pages.

Pagni, S. et al. (Jun. 1997). "Anastomotic Complications in Minimally Invasive Coronary Bypass Grafting," *Ann. Thorac. Surg.* 63(6 Suppl):S64-S67.

Palcic et al. (1991). "Lung Imaging Fluorescence Endoscope: A Device for Detection of Occult Lung Cancer," *Medical Design and Material*, thirteen pages.

Palcic, B. et al. (1990). "Development of a Lung Imaging Fluorescence Endoscope," *Annual International Conference of the IEEE Engineering in Medicine and Biology Society* 12(1):0196-0197.

Palcic, B. et al. (Aug. 1, 1990). "The Importance of Image Quality for Computing Texture Features in Biomedical Specimens," *Proc. SPIE* 1205:155-162.

Palcic, B. et al. (Jun. 1, 1991). "Lung Imaging Fluorescence Endoscope: Development and Experimental Prototype," *Proc. SPIE* 1448:113-117.

Palcic, B. et al. (Mar. 1991). "Detection and Localization of Early Lung Cancer by Imaging Techniques," *Chest* 99(3):742-743.

Paques, M. et al. (Mar. 2003). "Axon-Tracing Properties of Indocyanine Green," *Arch Ophthalmol.* 121(3):367-370.

Parungo, C.P. et al. (Apr. 2005). "Intraoperative Identification of Esophageal Sentinel Lymph Nodes with Near-Infrared Fluorescence Imaging," *The Journal of Thoracic and Cardiovascular Surgery* 129(4):844-850.

Parungo, C.P. et al. (Dec. 2004, e-published on Nov. 15, 2004). "In Vivo Optical Imaging of Pleural Space Drainage to Lymph Nodes of Prognostic Significance," *Annals of Surgical Oncology* 11(12):1085-1092.

Peak, M.J. et al. (1986). "DNA-to-Protein Crosslinks and Backbone Breaks Caused by FAR-and NEAR-Ultraviolet and Visible Light Radiations in Mammalian Cells," in *Mechanism of DNA Damage and Repair, Implications for Carcinogenesis and Risk Assessment*, SIMIC, M.G. (ed.) et al., Plenum Press, 233 Spring Street, New York, N.Y. 10013, pp. 193-202.

Peiretti et al. (2005). "Human Erythrocyte-Ghost-Mediated Choroidal Angiography and Photocoagulation," Database Biosis [online] Biosciences Information Service, Philadelphia, PA, US, XP002725023, Database Accession No. Prev200600056121, three pages, (Abstract only).

Peiretti, E. et al. (May 2005). "Human Erythrocyte-Ghost-Mediated Choroidal Angiography and Photocoagulation," *Investigative Ophthalmology & Visual Science*, ARVO Annual Meeting Abstract 46(13):4282, located at <http://iovs.arvojournals.org/article.aspx?articleid=2403707>, last visited on Oct. 7, 2016, two pages.

Perez, M.T. et al. (Sep. 2002). "In Vivo Studies on Mouse Erythrocytes Linked to Transferrin," *IUBMB Life* 54(3):115-121.

Pfister, A.J. et al. (Dec. 1992). "Coronary Artery Bypass Without Cardiopulmonary Bypass," *Ann. Thorac. Surg.* 54(6):1085-1092, (Discussion by S.R. Gundry).

Phillips, R.P. et al. (1991). "Quantification of Diabetic Maculopathy by Digital Imaging of the Fundus," *Eye* 5(1):130-137.

Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.

Profio, A.E. et al. (Jul.-Aug. 1984). "Fluorometer for Endoscopic Diagnosis of Tumors," *Medical Physics* 11(4):516-520.

Profio, A.E. et al. (Jun. 1, 1991). "Endoscopic Fluorescence Detection of Early Lung Cancer," *Proc. SPIE* 1426:44-46.

Profio, A.E. et al. (Sep.-Oct. 1986). "Digital Background Subtraction for Fluorescence Imaging," *Medical Physics* 13(5):717-721.

Profio, A.E. et al. (Nov./Dec. 1979). "Laser Fluorescence Bronchoscope for Localization of Occult Lung Tumors," *Medical Physics* 6:523-525.

Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," *Journal of Neuroscience Methods* 115(2):115-127.

Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.

Raabe et al. (2009, e-published on Nov. 12, 2008). "Laser Doppler Imaging for Intraoperative Human Brain Mapping", *NeuroImage* 44:1284-1289.

Raabe, A. et al. (Jan. 2003). "Near-Infrared Indocyanine Green Video Angiography: A New Method for Intraoperative Assessment of Vascular Flow," *Neurosurgery* 52(1):132-139.

Rava, R.P. et al. (Jun. 1, 1991). "Early Detection of Dysplasia in Colon and Bladder Tissue Using Laser-Induced Fluorescence," *Proc. SPIE* 1426:68-78.

Razum, N. et al. (Nov. 1987). "Skin Photosensitivity: Duration and Intensity Following Intravenous Hematoporphyrin Derivatives, HpD and DHE," *Photochemistry and Photobiology* 46(5):925-928.

Report on Observation by C2400-75i and ARGUS20 Under Low illumination conditions, Jan. 17, 2008.

Request for invalidation of Japanese Patent JP3881550 filed by Hamamatsu Photonics, Inc (with English Translation).

Reuthebuch, O et al. (Feb. 2004). "Novadaq SPY: Intraoperative Quality Assessment in Off Pump Coronary Artery Bypass Grafting," *Chest* 125(2):418-424.

Reuthebuch, O.T. et al. (May 2003). "Graft Occlusion After Deployment of the Symmetry Bypass System," *Ann. Thorac. Surg.* 75(5):1626-1629.

Richards-Kortum, R. et al. (Jun. 1991). "Spectroscopic Diagnosis of Colonic Dysplasia: Spectroscopic Analysis," *Biochemistry and Photobiology* 53(6):777-786.

(56) References Cited

OTHER PUBLICATIONS

Roberts, W.W. et al. (Dec. 1997). "Laparoscopic Infrared Imaging," *Surg. Endoscopy* 11(12):1221-1223.

Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.

Ropars, C. (ed.) et al. (1987). *Red Blood Cells as Carriers for Drugs. Potential therapeutic Applications*, Pergamon Press, Oxford, New York, pp. i-vii, (Table of Contents only).

Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.

Ross, G.L. et al. (Jul. 2004, e-published on Jun. 14, 2000). "Sentinel Node Biopsy in Head and Neck Cancer: Preliminary Results of a Multicenter Trial," *Annals of Surgical Oncology* 11(7):690-696.

Rossi, L. et al. (2001). "Erthrocyte-Mediated Delivery of Dexamethasone in Patients with Chronic Obstructive Pulmonary Disease," *Biotechnol. Appl. Biochem.* 33:85-89.

Rossi, L. et al. (1999). "Heterodimer-Loaded Erthrocytes as Bioreactors for Slow Delivery of the Antiviral Drug Azidothymidine and the Antimycobacterial Drug Ethambutol," *Aids Research and Human Retroviruses* 15(4):345-353.

Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.

Rozen, W.M. et al. (Jan. 2008). "Preoperative Imaging for DIEA Perforator Flaps: A Comparative Study of Computed Tomographic Angiography and Doppler Ultrasound," *Plastic and Reconstructive Surgery* 121(1):9-16.

Rubben, A. et al. (Mar. 1994). "Infrared Videoangiofluorography of the Skin with Indocyanine Green—Rat Random Cutaneous Flap Model and Results in Man," *Microvascular Research* 47(2):240-251.

Rubens, F.D. et al. (2002). "A New and Simplified Method for Coronary and Graft Imaging During CABG," *The Heart Surgery Forum* 5(2):141-144.

Sakatani, K. et al. (Nov. 1997). "Noninvasive Optical Imaging of the Subarachnoid Space and Cerebrospinal Fluid Pathways Based on Near Infrared Fluorescence," *J. Neurosurg.* 87(5):738-745.

Salmon, E.D. et al. (Oct. 1994). "High Resolution Multimode Digital Imaging System for Mitosis Studies In Vivo and In Vitro," *Biol. Bull* 187(2):231-232.

Sato, et al., (1991). "Development of a Visualization Method for the Microcirculation of deep viscera using an Infrared intravital microscope System," Research on ME Devices and ME Technology (with English Translation), five pages.

Satpathy G.R. et al. (Oct. 2004) "Loading Red Blood Cells with Trehalose: A Step Towards Biostabilization," *Cryobiology* 49(2):123-136.

Schaff, H.V. et al. (Oct. 15, 1996). "Minimal Thoracotomy for Coronary Artery Bypass: Value of Immediate Postprocedure Graft Angiography," *Supplement to Circulation* 94(8):I-51, (Abstract No. 0289), two pages.

Schellingerhout, D. et al. (Oct. 2000). "Quantitation of HSV Mass Distribution in a Rodent Brain Tumor Model," *Gene Therapy* 7(19):1648-1655.

Schmued, L. et al. (Aug. 27, 1990). "In Vivo Anterograde and Retrograde Axonal Transport of the Fluorescent Rhodamine-Dextran-Amine, Fluoro-Ruby, Within the CNS," *Brain Research* 526(1):127-134.

Schmued, L.C. et al. (Oct. 29, 1993). "Intracranial Injection of Fluoro-Gold Results in the Degeneration of Local but not Retrogradely Labeled Neurons," *Brain Research* 626(1-2):71-77.

Schneider Jr., H.C. et al. (Jan. 1975). "Fluorescence of Testicle, An Indication of Viability of Spermatic Cord After Torsion" *Urology* V(1):133-136.

Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.

Sekijima, M. et al. (Sep. 2004). "An Intraoperative Fluorescent Imaging System in Organ Transplantation," *Transplantation Proceedings* 36(7):2188-2190.

Serov, A. et al. (Mar. 1, 2002). "Laser Doppler Perfusion Imaging with a Complimentary Metal Oxide Semiconductor Image Sensor," *Optics Letters* 27(5):300-302.

Serov, A.N. et al. (Sep. 23, 2003). "Quasi-Parallel Laser Doppler Perfusion Imaging Using a CMOS Image Sensor," *Proc. SPIE* 5067:73-84.

Sherif, A. et al. (Sep. 2001). "Lymphatic Mapping and Detection of Sentinel Nodes in Patients with Bladder Cancer," *The Journal of Urology* 166(3):812-815.

Sheth, S.A. et al. (Apr. 22, 2004) "Linear and Nonlinear Relationships between Neuronal Activity, Oxygen Metabolism, and Hemodynamic Responses," *Neuron* 42(2):347-355.

Shoaib, T. et al. (Jun. 1, 2001). "The Accuracy of Head and Neck Carcinoma Sentinel Lymph Node Biopsy in the Clinically N0 Neck," *Cancer* 91(11):2077-2083.

Siemers, B.M. et al. (Nov. 2001). "The Acoustic Advantage of Hunting at Low Heights Above Water: Behavioual Experiments on the European 'Trawling' Bats Myotis Capaccinii, M Dasycneme and M. Daubentonii," *J. Eperimental Biol.*204(Pt. 22):3843-3854.

Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.

Slakter, J.S. et al. (Jun. 1995). "Indocyanine-Green Angiography," *Current Opinion in Ophthalmology* 6(III):25-32.

Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.

Soltesz, E.G. et al. (Jan. 2005). "Intraoperative Sentinel Lymph Node Mapping of the Lung Using Near-Infrared Fluorescent Quantum Dots," *Ann. Thorac. Surg.* 79(1):269-277.

Staurenghi, G. et al. (Dec. 2001). "Combining Photodynamic Therapy and Feeder Vessel Photocoagulation: A Pilot Study," *Seminars in Ophthalmology* 16(4):233-236.

Stern, M.D. (Mar. 6, 1975). "In Vivo Evaluation of Microcirculation by Coherent Light Scattering," *Nature* 254(5495):56-58.

Still, J. et al. (Mar. 1999). "Evaluation of the Circulation of Reconstructive Flaps Using Laser-Induced Fluorescence of Indocyanine Green," *Ann. Plast. Surg.* 42(3):266-274.

Still, J.M. et al. (Jun. 2001). "Diagnosis of Burn Depth Using Laser-Induced Indocyanine Green Fluorescence: A Preliminary Clinical Trial," *Burns* 27(4):364-371.

Stoeckli, S.J. et al. (Sep. 2001). "Sentinel Lymph Node Evaluation in Squamous Cell Carcinoma of the Head and Neck," *Otolaryngol. Head Neck Surg.* 125(3):221-226.

Subramanian, V.A. et al. (Oct. 15, 1995). "Minimally Invasive Coronary Bypass Surgery: A Multi-Center Report of Preliminary Clinical Experience," *Supplement to Circulation* 92(8):I-645, (Abstract No. 3093), two pages.

Sugi, K. et al. (Jan. 2003). "Comparison of Three Tracers for Detecting Sentinel Lymph Nodes in Patients with Clinical N0 Lung Cancer," *Lung Cancer* 39(1):37-40.

Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.

Suma, H. et al. (2000). "Coronary Artery Bypass Grafting Without Cardiopulmonary Bypass in 200 Patients," *J. Cardiol.* 36(2):85-90, (English Abstract only).

Taggart, D.P. et al. (Mar. 2003). "Preliminary Experiences with a Novel Intraoperative Fluorescence Imaging Technique to Evaluate the Patency of Bypass Grafts in Total Arterial Revascularization," *Ann Thorac Surg.* 75(3):870-873.

(56) References Cited

OTHER PUBLICATIONS

Taichman, G.C. et al. (Jun. 1987). "The Use of Cardio-Green for Intraoperative Visualization of the Coronary Circulation: Evaluation of Myocardial Toxicity," *Texas Heart Institute Journal* 14(2):133-138.

Takahashi, M. et al. (Sep. 2004). "SPY: An Innovative Intra-Operative Imaging System to Evaluate Graft Patency During Off-Pump Coronary Artery Bypass Grafting," *Interactive Cardio Vascular and Thoracic Surgery* 3(3):479-483.

Takayama, T. et al. (Apr. 1992). "Intraoperative Coronary Angiography Using Fluorescein Basic Studies and Clinical Application," *Vascular and Endovascular Surgery* 26(3):193-199.

Takayama, T. et al. (Jan. 1991). "Intraoperative Coronary Angiography Using Fluorescein" *The Annals of Thoracic Surgery* 51(1):140-143.

Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.

Tang, G.C. et al. (1989). "Spectroscopic Differences between Human Cancer and Normal Lung and Breast Tissues," *Lasers in Surgery and Medicine* 9(3):290-295.

Taylor,, K.M. (Apr. 1998). "Brain Damage During Cardiopulmonary Bypass," *Annals of Thoracic Surgery* 65(4):520-526.

The American Heritage Medical Dictionary. "Perfuse." p. 401 (2008), three pages.

Thelwall, P.E. et al. (Oct. 2002). "Human Erythrocyte Ghosts: Exploring the Origins of Multiexponential Water Diffusion in a Model Biological Tissue with Magnetic Resonance," *Magnetic Resonance in Medicine* 48(4):649-657.

Torok, B. et al. (May 1996). "Simultaneous digital indocyanine green and fluorescein angiography" *Klinische Monatsblatter Fur Augenheilkunde* 208(5):333-336.

Tsutsumi, D. et al. "Moisture Detection of road surface using infrared camera," Reports of the Hokkaido Industrial Research Institute (No. 297), Issued on Nov. 30, 1998, two pages.

Tubbs, R.S. et al. (Apr. 2005). "Anatomic Landmarks for Nerves of the Neck: A Vade Mecum for Neurosurgeons," *Neurosurgery* 56(2 Suppl.):ONS256-ONS260, (2005).

Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.

Uren, R.F. (Jan. 2004). "Cancer Surgery Joins the Dots," *Nature Biotechnology* 22(1):38-39.

Valero-Cabré, A. et al. (Jan. 15, 2001). "Superior Muscle Reinnervation after Autologous Nerve Graft or Poly-L-Lactide-ε-Caprolactone (PLC) Tube Implantation in Comparison to Silicone Tube Repair," *Journal of Neuroscience Research* 63(2):214-223.

Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.

Wachi, A. et al. (Apr. 1995). "Characteristics of Cerebrospinal Fluid Circulation in Infants as Detected With MR Velocity Imaging," *Child's Nerv System* 11(4):227-230.

Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.

Weinbeer, M. et al. (Nov. 25, 2013). "Behavioral Flexibility of the Trawling Long-Legged Bat, Macrophyllum Macrophyllum (Phyllostomidae)," *Frontiers in Physiology* 4(Article 342):1-11.

What is Perfusion? A Summary of Different Typed of Perfusion. (Sep. 1, 2004). Located at, http://www.perfusion.com/cgi-bin/absolutenm/templates/articledisplay.asp?articleid=1548#.Vo8Hv02FPGj, last visited on Jan. 7, 2016, two pages.

Wise, R.G. et al. (Nov. 2005). "Simultaneous Measurement of Blood and Myocardial Velocity in the Rat Heart by Phase Contrast MRI Using Sparse q-Space Sampling" *Journal of Magnetic Resonance Imaging* 22(5):614-627.

Woitzik, J. et al. (Apr. 2005). "Intraoperative Control of Extracranial-Intracranial Bypass Patency by Near-Infrared Indocyanine Green Videoangiography," *J. Neurosurg.*102 (4):692-698.

Wollert, H.G. et al. (Dec. 1989). "Intraoperative Visualization of Coronary Artery Fistula Using Medical Dye," *The Thoracic and Cardiovascular Surg.* 46(6):382-383.

Wu, C. et al. (Apr. 15, 2005). "cGMP (Guanosine 3',5'-Cyclic Monophosphate) Transport Across Human Erythrocyte Membranes," *Biochemical Pharmacology* 69(8):1257-1262.

Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.

Yoneya, S. et al. (Jun. 1998). "Binding Properties of Indocyanine Green in Human Blood," *IOVS* 39(7):1286-1290.

Yoneya, S. et al. (Sep. 1993). "Improved Visualization of the Choroidal Circulation with Indocyanine Green Angiography," *Arch Opthalmol.* 111(9):1165-1166.

Young. I.T. et al. (1993). "Depth of Focus in Microscopy," SCIA '93, Proc. Of the 8th Scandinavian Conference on Image Analysis, Tromso, Norway, pp. 493-498, six pages.

Chinese Third Office Action mailed Aug. 8, 2016 for Chinese Application No. 201180057244.8 filed on Sep. 20, 2011, eighteen pages.

EP Communication in pursuant to Article 94(3) EPC mailed Mar. 9, 2016 for European Patent Application No. 09739980.2 filed May 1, 2009.

European Communication pursuant to Article 94(3) mailed on May 27, 2016 for EP Application No. 15160177.0 filed on Aug. 11, 2000, five pages.

European Decision in Opposition Proceeding Revoking (Jun. 10, 2010). European Patent No. 1 143 852, thirty pages.

European Opposition of European Patent No. EP1143852 lodged by Hamamatsu Photonics, Inc., Jul. 30, 2008, forty pages.

Extended European Search Report mailed Oct. 14, 2015 for EP Application No. 13806313.6 filed on Jun. 20, 2013, nine pages.

Final Office Action mailed on Apr. 10, 2008, for U.S. Appl. No. 11/106,154, filed Apr. 14, 2005, six pages.

Final Office Action mailed on Apr. 2, 2013, for U.S. Appl. No. 13/419,368, filed Mar. 13, 2012, five pages.

Final Office Action mailed on Apr. 20, 2016, for U.S. Appl. No. 14/543,429, filed Nov. 17, 2014, seven pages.

Final Office Action mailed on Apr. 27, 2011 for U.S. Appl. No. 11/515,419, filed Sep. 1, 2006, nine pages.

Final Office Action mailed on Aug. 10, 2012, for U.S. Appl. No. 11/912,877, filed Aug. 13, 2008, ten pages.

Final Office Action mailed on Dec. 31, 2015 for U.S. Appl. No. 14/177,050 filed Feb. 10, 2014, eighteen pages.

Final Office Action mailed on Dec. 4, 2014, for U.S. Appl. No. 12/776,835, filed May 10, 2010, thirteen pages.

Final Office Action mailed on Feb. 1, 2013, for U.S. Appl. No. 12/776,835, filed May 10, 2010, thirteen pages.

Final Office Action mailed on Feb. 13, 2015, for U.S. Appl. No. 14/543,429, filed Nov. 17, 2014, six pages.

Final Office Action mailed on Feb. 18, 2010, for U.S. Appl. No. 11/106,154, filed Apr. 14, 2005, six pages.

Final Office Action mailed on Feb. 4, 2015 for U.S. Appl. No. 13/314,418, filed Dec. 8, 2011, six pages.

Final Office Action mailed on Jul. 21, 2016 for U.S. Appl. No. 14/543,356, filed Nov. 17, 2014, seven pages.

Final Office Action mailed on Jul. 9, 2015, for U.S. Appl. No. 14/543,356, filed Nov. 17, 2014, eight pages.

Final Office Action mailed on Jun. 1, 2015, for U.S. Appl. No. 14/543,429, filed Nov. 17, 2014, nine pages.

Final Office Action mailed on Jun. 13, 2014, for U.S. Appl. No. 12/776,835, filed May 10, 2010, thirteen pages.

Final Office Action mailed on Mar. 28, 2013, for U.S. Appl. No. 12/063,349, filed May 12, 2010, twenty pages.

Final Office Action mailed on Nov. 6, 2013, for U.S. Appl. No. 13/419,368, filed Mar. 13, 2012, five pages.

Final Office Action mailed on Oct. 7, 2011 for U.S. Appl. No. 11/851,312, filed Sep. 6, 2007, ten pages.

(56) References Cited

OTHER PUBLICATIONS

Final Office Action mailed on Sep. 13, 2011, for U.S. Appl. No. 11/106,154, filed Apr. 14, 2005, five pages.
Final Office Action mailed on Sep. 17, 2014 for U.S. Appl. No. 11/515,419, filed Sep. 1, 2006, eleven pages.
Final Office Action mailed on Sep. 23, 2004, for U.S. Appl. No. 09/744,034, filed Apr. 27, 2001, seven pages.
Final Office Action mailed on Sep. 29, 2016, for U.S. Appl. No. 13/922,996, filed Jun. 20, 2013, fourteen pages.
Indian Examination Report mailed on Sep. 22, 2016 for Indian Application No. 7566/DELNP/2010, filed on Oct. 27, 2010, nine pages.
International Preliminary Examination Report completed on Jul. 1, 2001 for PCT/US00/22088, filed on Aug. 11, 2000, three pages.
International Search Report and Written Opinion mailed Jul. 29, 2009 for PCT/US2009/043975 filed on May 14, 2009, eleven pages.
International Search Report mailed on Jun. 2, 2009 for PCT Application No. PCT/EP2008/008547, filed on Oct. 9, 2008, five pages.
International Search Report mailed Dec. 3, 2015 for PCT Application No. PCT/CA2015/050973 filed on Sep. 28, 2015, three pages.
International Search Report mailed on Jan. 22, 2014, for PCT Application No. PCT/IB2013/001934, filed on Jun. 20, 2013, four pages.
International Search Report mailed on Oct. 18, 2000, for PCT Application No. PCT/US2000/22088, filed on Aug. 11, 2000, one page.
International Search Report mailed on Sep. 11, 2009 for Application No. PCT/US2009/042606 filed on May 1, 2009, five days.
Japanese First Office Action mailed Feb. 1, 2016 for Japanese Patent Application No. 2015-517876 filed Jun. 20, 2013, eight pages.
Korean Patent Office, Office Action mailed Jun. 25, 2014 in Korean Patent Application No. 10-2013-7035027 w/English-language Translation, fifteen pages.
Non-Final Office Action mailed on Apr. 26, 2012, for U.S. Appl. No. 12/776,835, filed May 10, 2010, nine pages.
Non-Final Office Action mailed on Apr. 28, 2010, for U.S. Appl. No. 11/946,672, filed Nov. 28, 2007, nine pages.
Non-Final Office Action mailed on Aug. 10, 2016 for U.S. Appl. No. 14/177,050, filed Feb. 10, 2014, twenty pages.
Non-Final Office Action mailed on Aug. 29, 2014 for U.S. Appl. No. 12/063,349, filed May 12, 2010, nineteen pages.
Non-Final Office Action mailed on Dec. 30, 2010, for U.S. Appl. No. 11/106,154, filed Apr. 14, 2005, six pages.
Non-Final Office Action mailed on Feb. 1, 2011 for U.S. Appl. No. 11/851,312, filed Sep. 6, 2007, seven pages.
Non-Final Office Action mailed on Feb. 5, 2016, for U.S. Appl. No. 14/543,356, filed Nov. 17, 2014, seven pages.
Non-Final Office Action mailed on Jan. 22, 2014 for U.S. Appl. No. 11/851,312, filed Sep. 6, 2007, ten pages.
Non-Final Office Action mailed on Jan. 27, 2012, for U.S. Appl. No. 11/912,877, filed Aug. 13, 2008, eleven pages.
Non-Final Office Action mailed on Jan. 9, 2009, for U.S. Appl. No. 11/106,154, filed Apr. 14, 2005, six pages.
Non-Final Office Action mailed on Jul. 2, 2015, for U.S. Appl. No. 14/177,050, filed Feb. 10, 2014, nineteen pages.
Non-Final Office Action mailed on Jul. 22, 2015 for U.S. Appl. No. 13/314,418, filed Dec. 8, 2011, six pages.
Non-Final Office Action mailed on Jul. 8, 2014 for U.S. Appl. No. 13/314,418, filed Dec. 8, 2011, seven pages.
Non-Final Office Action mailed on Jun. 11, 2013 for U.S. Appl. No. 11/515,419, filed Sep. 1, 2006, eleven pages.
Non-Final Office Action mailed on Jun. 28, 2012 for U.S. Appl. No. 12/063,349, filed May 12, 2010, seventeen pages.
Non-Final Office Action mailed on Mar. 10, 2004, for U.S. Appl. No. 09/744,034, filed Apr. 27, 2001, seven pages.
Non-Final Office Action mailed on Mar. 13, 2015, for U.S. Appl. No. 14/543,356, filed Nov. 17, 2014, eight pages.
Non-Final Office Action mailed on Mar. 6, 2007, for U.S. Appl. No. 11/106,154, filed Apr. 14, 2005, eight pages.
Non-Final Office Action mailed on May 21, 2015, for U.S. Appl. No. 13/922,996, filed Jun. 20, 2013, fourteen pages.
Non-Final Office Action mailed on May 6, 2015 for U.S. Appl. No. 12/063,349, filed May 12, 2010, seventeen pages.
Non-Final Office Action mailed on Nov. 27, 2015, for U.S. Appl. No. 14/543,429, filed Nov. 17, 2014, six pages.
Non-Final Office Action mailed on Nov. 9, 2015, for U.S. Appl. No. 14/177,045, filed Feb. 10, 2014, seven pages.
Non-Final Office Action mailed on Oct. 3, 2013, for U.S. Appl. No. 12/776,835, filed May 10, 2010, twelve pages.
Non-Final Office Action mailed on Sep. 15, 2010, for U.S. Appl. No. 11/106,154, filed Apr. 14, 2005, six pages.
Non-Final Office Action mailed on Sep. 30, 2010 for U.S. Appl. No. 11/515,419, filed Sep. 1, 2006, eleven pages.
Non-Final Office Action mailed on Sep. 5, 2012 for U.S. Appl. No. 12/933,477, filed Sep. 20, 2010, seven pages.
Notice of Allowance mailed Jul. 13, 2016 for U.S. Appl. No. 14/598,832, filed Jan. 16, 2015, seven pages.
Notice of Allowance mailed on Apr. 17, 2014, for U.S. Appl. No. 13/419,368, filed Mar. 13, 2012, five pages.
Notice of Allowance mailed on Mar. 7, 2005, for U.S. Appl. No. 09/744,034, filed Apr. 27, 2001, five pages.
Notice of Allowance mailed on May 26, 2016, for U.S. Appl. No. 14/177,045, filed Feb. 10, 2014, eight pages.
Notice of Allowance mailed on Nov. 25, 2015, for U.S. Appl. No. 14/598,832, filed Jan. 16, 2015, seven pages.
Notice of Allowance mailed on Nov. 30, 2010, for U.S. Appl. No. 11/946,672, filed Nov. 28, 2007, six pages.
Notice of Allowance mailed on Oct. 4, 2013, for U.S. Appl. No. 11/912,877, filed Aug. 13, 2008, nine pages.
Notice of Allowance mailed on Oct. 6, 2014, for U.S. Appl. No. 13/419,368, filed Mar. 13, 2012, five pages.
Notification of Transmittal of International Search Report and the Written Opinion of the International Searching Authority, or the Declaration mailed on Apr. 3, 2008 for PCT/US07/77892, filed on Sep. 7, 2007, ten pages.
Partial European Search Report mailed on Dec. 16, 2010 for European Application No. 10186218.3 filed on Aug. 11, 2000, seven pages.
Partial European Search Report mailed on Jun. 11, 2014 for European Application No. 13178642.8, filed on May 1, 2009, five pages.
Supplemental European Search Report for EP Application No. 00955472.6 mailed on Jul. 6, 2004, five pages.
Written Opinion for Application No. PCT/EP2008/008547, mailed on Jun. 2, 2009; eleven pages.
Written Opinion of the International Searching Authority mailed on Jan. 22, 2014, for PCT Application No. PCT/IB2013/001934, filed on Jun. 20, 2013, six pages.

METHOD FOR EVALUATING BLUSH IN MYOCARDIAL TISSUE

CROSS-REFERENCE TO RELATED APPLICATIONS

This application is a divisional of U.S. application Ser. No. 13/850,063, filed Mar. 25, 2013, now U.S. Pat. No. 8,965,488, which is a divisional of U.S. application Ser. No. 12/841,659, now U.S. Pat. No. 8,406,860, which is a continuation-in-part of PCT International Application No. PCT/CA2009/00073, filed Jan. 23, 2009, which claims the benefit of U.S. Provisional Application No. 61/023,818, filed Jan. 25, 2008, the entire contents of which are incorporated herein by reference. This application also claims the benefit of prior filed U.S. Provisional Application No. 61/243,688, filed Sep. 18, 2009, the entire contents of which are incorporated herein by reference.

BACKGROUND OF THE INVENTION

The invention relates to a method for evaluating myocardial blush in tissue from images recorded following injection of fluorescent dyes.

TIMI (Thrombolysis In Myocardial Infarction) studies initially suggested that successful restoration of flow in an infarcted artery was the major goal of reperfusion. However, substantial evidence has grown over the years showing that distortion of microvasculature and myocardial perfusion is often present despite epicardial artery patency. This might be the result of a combination of distal embolization and reperfusion injury with cellular and extracellular edema, neutrophil accumulation and release of detrimental oxygen free radicals.

Myocardial blush was first defined by van't Hof et al. as a qualitative visual assessment of the amount of contrast medium filling a region supplied by an epicardial coronary artery. It is graded as Myocardial Blush Grade: 0 (=no myocardial blush or contrast density), 1 (=minimal myocardial blush or contrast density), 2 (=myocardial blush or contrast density which exists to lesser extent and its clearance is diminished compared to non-infarct-related coronary artery), and 3 (=normal myocardial blush or contrast density comparable with that obtained during angiography of a contralateral or ipsilateral non-infarct-related coronary artery). When myocardial blush persists (long "wash-out rate" or "staining"), it suggests leakage of the contrast medium into the extravascular space or impaired venous clearance and is graded 0.

The consequences of microvascular damage are extremely serious. In patients treated with thrombolytics for acute myocardial infarction, impaired myocardial perfusion as measured by the myocardial blush score corresponds to a higher mortality, independent of epicardial flow. Myocardial blush grade correlates significantly with ST segment resolution on ECGs, enzymatic infarct size, LVEF, and is an independent predictor of long-term mortality. Myocardial blush grade may be the best invasive predictor of follow-up left ventricular function. Determining the myocardial blush has emerged as a valuable tool for assessing coronary microvasculature and myocardial perfusion in patients undergoing coronary angiography and angioplasty.

The degree of blush that appears during imaging (e.g., imaging with a fluorescent dye, such as ICG) is directly related to the underlying tissue perfusion. Conventionally, to quantitatively characterize kinetics of dye entering the myocardium using the angiogram, digital subtraction angiography (DSA) has been utilized to estimate the rate of brightness (gray/sec) and the rate of growth of blush (cm/sec). DSA is performed at end diastole by aligning cine frame images before the dye fills the myocardium with those at the peak of a myocardial filling to subtract spine, ribs, diaphragm, and epicardial artery. A representative region of myocardium is sampled that is free of overlap by epicardial arterial branches to determine the increase in the grayscale brightness of the myocardium at peak intensity. The circumference of the myocardial blush is then measured using a handheld planimeter. The number of frames required for the myocardium to reach peak brightness is converted into time by dividing the frame count by the frame rate. This approach is quite time-consuming and is difficult to perform on a beating heart and to conclude within a reasonable time.

Generally, conventional techniques gathering statistical information about a ROI rely on algorithms that track the ROI during movement of the underlying anatomy and attempt to keep the ROI localized in the same tissue portion. For example, the user can draw an initial ROI in the image, ignoring any blood vessels not to be included in the calculation, with the initial ROI then adjusted to the moving anatomy through linear translation, rotation, and distortion. However, this approach is computationally intensive and not reliable with low contrast images.

Accordingly, there is a need for a method to determine blush of myocardial tissue while the heart is beating, to eliminate effects from features other than myocardial tissue that may migrate into the region of interest (blood vessels, clips, the surgeon's hands, etc. . . . ), and to produce useful information for the surgeon during a medical procedure within a "reasonable time," if not within "real time."

There is also a need for measuring improvement in cardiac function by measuring the time differential between when contrast in a blood vessel reaches its peak intensity and when the contrast in a neighboring region in the myocardial tissue reaches its corresponding peak. If this time differential decreases after a medical procedure as compared to before the procedure, under uniform hemodynamic conditions cardiac function can be said to have improved. A method for tracking blood vessels during image acquisition improves our ability to locate the time at which the contrast in a blood vessel achieves its peak intensity.

SUMMARY OF THE INVENTION

The present invention is directed to a method for evaluating myocardial blush in tissue from images recorded following injection of fluorescent dyes using a static ROI (Region-of-Interest) that is fixed in position on the image while the heart (or other tissue of interest) moves under it in the image sequence. The static ROI uses a statistical technique to eliminate intensity outliers and to evaluate only those pixels that have less inter-pixel intensity variance. The technique is highly robust, and the results depend only insignificantly on changes to the ROI size and position, providing the ROI is placed in the same general region of the anatomy.

According to one aspect of the invention, a method for determining perfusion in myocardial tissue using fluorescence imaging, includes the steps of defining a static region of interest (ROI) in an image of the myocardial tissue, measuring fluorescence intensity values of image elements (pixels) located within the ROI, and determining a blush value from an average of the intensity values of image elements located within a smallest contiguous range of image intensity values containing a first predefined fraction of a total measured image intensity of all image elements within the ROI.

Advantageous embodiments may include one or more of the following features. The smallest range of contiguous image intensity values may be determined from a histogram of a frequency of occurrence of the measured image intensity values, wherein the first predefined fraction may be between 70% and 30%, preferably between 60% and 40%, and most preferably at about 50%. Blush values are determined, optionally continuously, over a predefined period of time. At least one of the blush rate and the washout rate may be determined from the slope of the time-dependent blush values.

Alternatively or in addition, the blush and associated perfusion may be determined by defining a second static ROI in the image of the myocardial tissue, with the second ROI including an arterial blood vessel, and determining a measure of the peak intensity of the arterial blood vessel from a total intensity of the intensity values of image elements located within a smallest contiguous range of high image intensity values containing a second predefined fraction, for example 20%, of a total measured image intensity of brightest image elements within the ROI. This measurement can then be used to determine an outcome of a procedure by comparing an elapsed time between a maximum blush value and maximum measure of perfusion before the procedure and an elapsed time between a maximum blush value and maximum measure of perfusion after the procedure.

According to another aspect of the invention, a method for tracking a blood vessel in an image includes the steps of (a) acquiring a fluorescence image of tissue containing a blood vessel, (b) delimiting a segment of the blood vessel with boundaries oriented substantially perpendicular to a longitudinal direction of the blood vessel, (c) constructing at least one curve extending between the delimiting boundaries and located within lateral vessel walls of the blood vessel, wherein the at least one curve terminates at the delimiting boundaries substantially perpendicular to the boundaries, and (d) determining a fluorescence signal intensity in the fluorescence image along the at least one curve, with the signal intensity being representative of vessel perfusion.

In one exemplary embodiment, the at least one curve may be defined by a spline function. For example, more than one curve may be constructed and the fluorescence signal intensity may be determined by averaging the signal intensity from points on the curves having a substantially identical distance from one of the delimiting boundaries.

Advantageously, the position of the lateral vessel walls in the fluorescence image may be determined using an edge-detection algorithm, such as a Laplacian-of-a-Gaussian operator.

In another exemplary embodiment, time-sequential fluorescence images of the tissue containing the blood vessel may be acquired. Characteristic dimensions of the delimited segment may then be determined from the location of the lateral vessel walls in the first image, and positions of lateral vessel walls may be determined in at least one second image. The characteristic dimensions from the first image may then be matched to the positions of lateral vessel walls in the second image to find a location of the lateral vessel walls of the first image in the at least one second image. The steps (c) and (d) above are then repeated for the second image or images.

Advantageously, an average fluorescence signal intensity of all points may be computed along the curve and a change in perfusion of the blood vessel may be determined from a change in the average fluorescence signal intensity between the time-sequential images.

These and other features and advantages of the present invention will become more readily appreciated from the detailed description of the invention that follows and from the appended drawings.

DETAILED DESCRIPTION OF EXEMPLARY EMBODIMENTS

Figure 1:
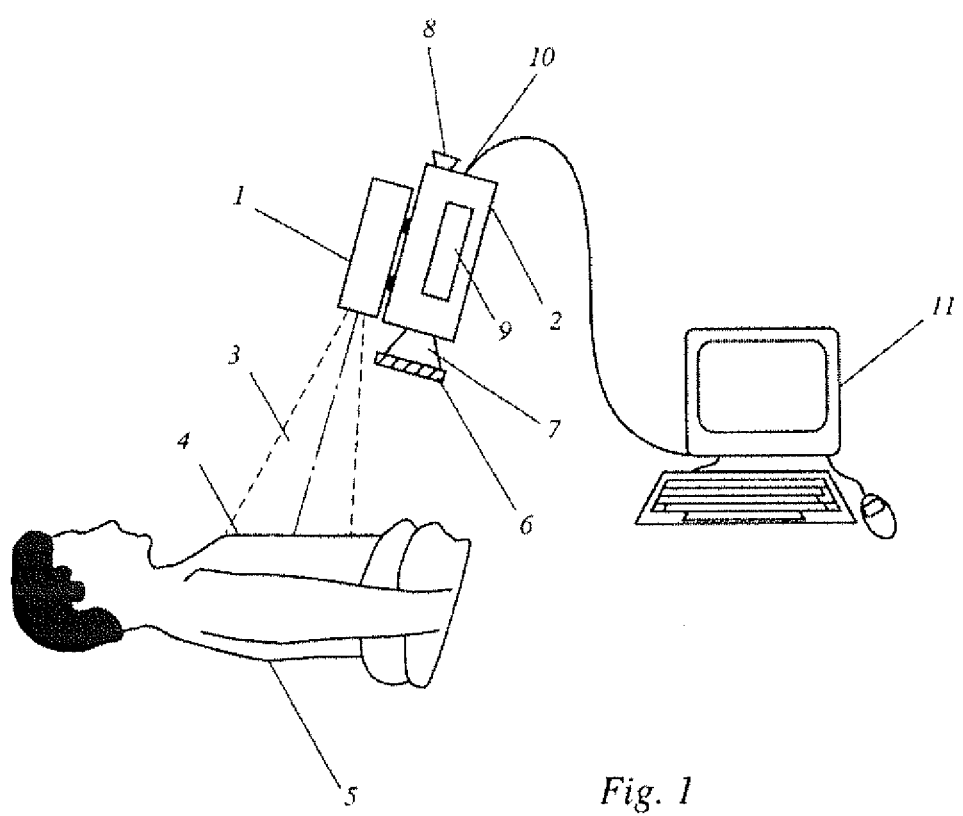
FIG. 1 shows schematically a camera system for observing ICG fluorescence.

FIG. 1 shows schematically a device for non-invasively determining blush of myocardial tissue by ICG fluorescence imaging. An infrared light source, for example, one or more diode lasers or LEDs, with a peak emission of about 780-800 nm for exciting fluorescence in ICG is located inside housing 1. The fluorescence signal is detected by a CCD camera 2 having adequate near-IR sensitivity; such cameras are commercially available from several vendors (Hitachi, Hamamatsu, etc.). The CCD camera 2 may have a viewfinder 8, but the image may also be viewed during the operation on an external monitor which may be part of an electronic image processing and evaluation system 11.

A light beam 3, which may be a divergent or a scanned beam, emerges from the housing 1 to illuminate an area of interest 4, i.e. the area where the blush of myocardial tissue is to be measured. The area of interest may be about 10 cm×10 cm, but may vary based on surgical requirements and the available illumination intensity and camera sensitivity.

A filter 6 is typically placed in front of the camera lens 7 to block excitation light from reaching the camera sensor, while allowing fluorescence light to pass through. The filter 6 may be an NIR long-wave pass filter (cut filter), which is only transparent to wavelengths greater than about 815 nm, or preferably a bandpass filter transmitting at peak wavelengths of between about 830 and about 845 nm and having a full width at half maximum (FWHM) transmission window of between about 10 nm and 25 nm in order to block the excitation wavelength band. The camera 2 may also be designed to acquire a color image of the area of interest to allow real-time correlation between the fluorescence image and the color image.

In general, the surgeon is interested in how well the blood is perfusing the tissue in the area within a region of interest (ROI). Blood vessels visible in the image typically include major blood vessels, e.g., arteries; however, arterial blood flow may not be of interest to the surgeon when considering perfusion of the surrounding myocardial tissue. Because these blood vessels may have either a higher or a lower brightness in the image, depending on the phase of the cardiac cycle, contributions from blood vessels to the measured image brightness may alter the myocardial blush grade by skewing the average image brightness upward or downward. In order to obtain a correct value for the myocardial blush, the contributions from the blood vessels must be eliminated before the blush grade is computed.

Figure 2:
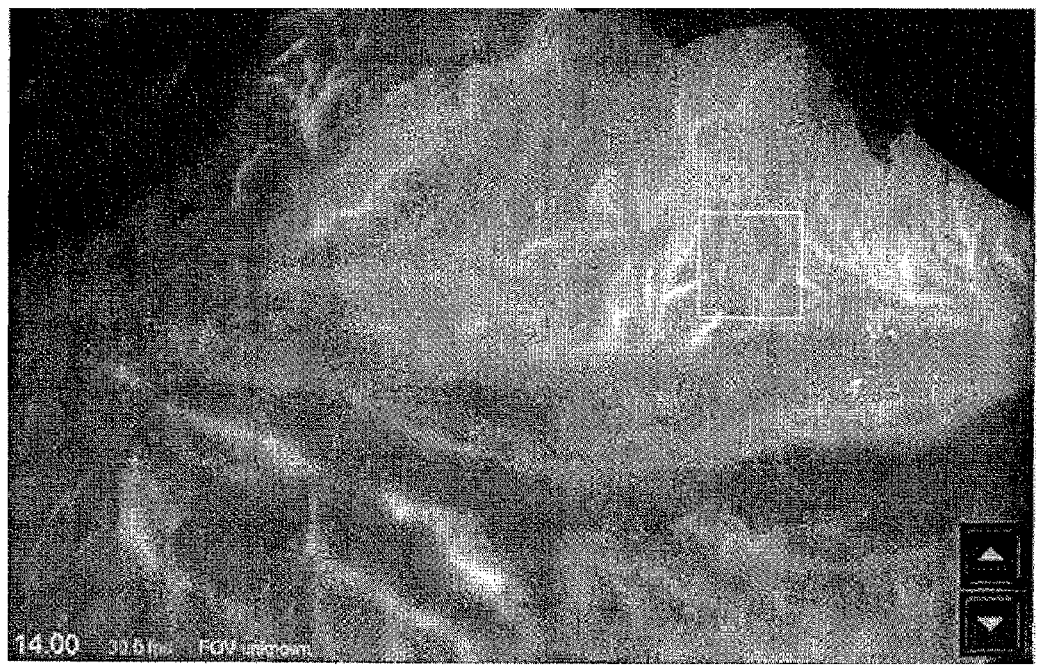
FIG. 2 shows an ICG fluorescent cardiac image, with the rectangle delineating a static ROI on the imaged area.

FIG. 2 shows a typical ICG fluorescent image of a heart showing blood vessels and myocardial tissue, with a rectangle delineating a static ROI on the imaged area. The ROI is static, meaning that it does not track tissue movement when the heart is beating. This simplifies the computation, while the results computed with the method of the invention are robust and largely insensitive to tissue movement.

To compute meaningful average blush intensity within the delineated static ROI, the following needs to be taken into consideration:
 1 The selected area of the anatomy within the ROI should consist primarily of myocardial tissue, while minimizing the effects from blood vessels, clips, etc. that appear in the ROI and may move in and out of the ROI when the heart is beating.
 2 The measured myocardial blush value should be substantially independent of the size of the ROI in the selected area of the anatomy.

Figure 3:
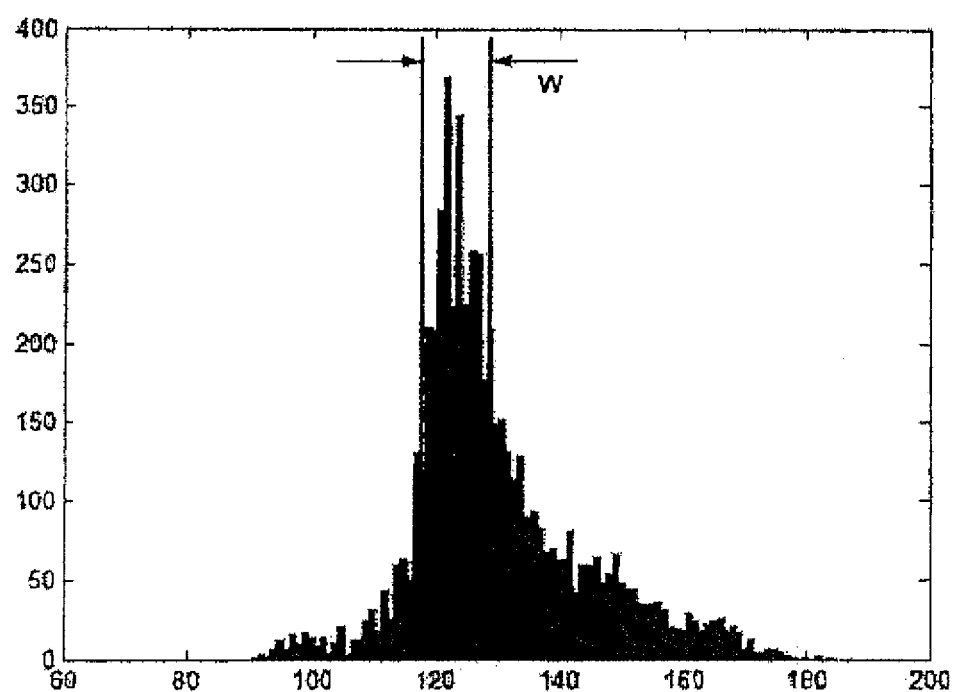
FIG. 3 shows a histogram of the number of pixels (vertical axis) as a function of the measured brightness value (horizontal axis)

According to one embodiment illustrated in FIG. 3, a histogram of the grayscale intensity values in the ROI of FIG. 2 is generated. The horizontal axis of the histogram represents the full range of intensity values arranged in bins (e.g., $2^8=256$ bins for an 8-bit image representing pixel intensities 0 to 255), whereas the vertical axis indicates the number of pixels for each intensity value in a bin. In comparison, a histogram of a 12-bit image would have $2^{12}=4,096$ intensity bins.

A sliding window W is applied across the abscissa, and the smallest set of adjacent histogram bins containing in excess of a predetermined percentage of the total intensity is determined. In the illustrated example, a percentage value of 50% is selected as criterion for the bins to be included, although other values can be selected as long as these selected values exclude outliers and provide a reliable assessment of the blush. For the histogram depicted in FIG. 3, the smallest set of adjacent histogram bins containing at least 50% of the intensity counts results in a window W which is 12 bins wide and includes the intensity values between 120 and 131.

The average intensity for the static ROI is then computed using only the values inside the window determined above, i.e., the number of pixels in a bin multiplied with the intensity in that bin and summed over all bins within the window W.

This approach excludes the intensity outliers (both low and high intensity values) from the computation of the average intensity representing the myocardial blush value in the ROI. In other words, only intensity values between 120 and 131 within the ROI are included in the subsequent calculation.

Figure 4:
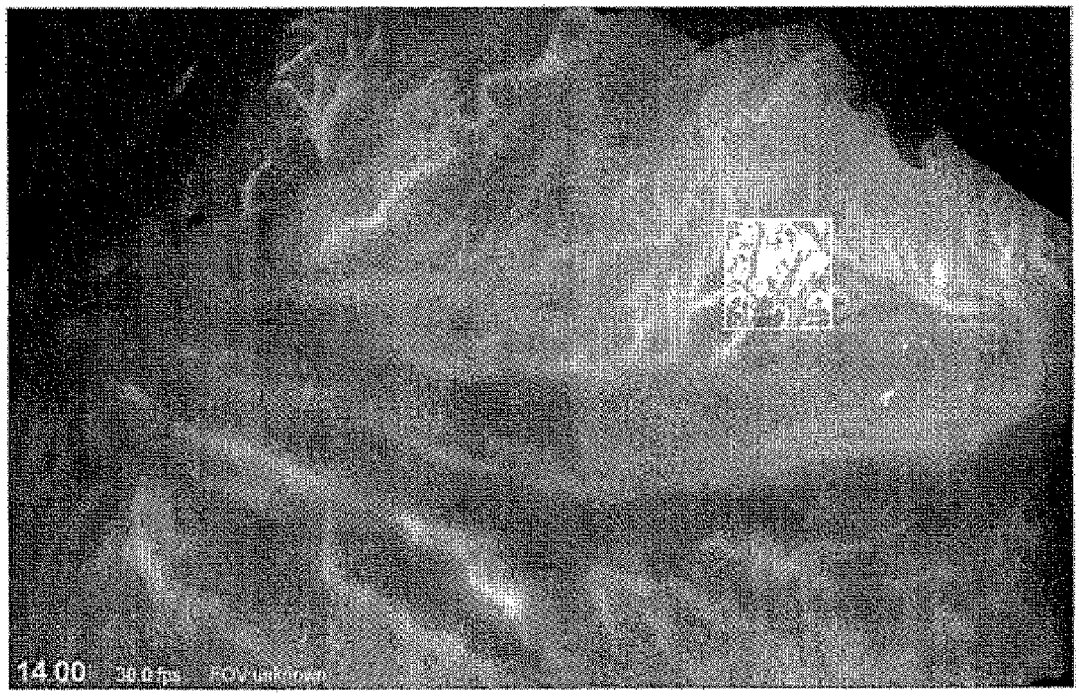
FIG. 4 shows the location of pixels within the static ROI that contain at least 50% of the intensity counts over the smallest set of adjacent histogram bins in FIG. 3.

FIG. 4 shows the location of pixels within the static ROI with intensity values within the window W (according to the selection criterion that about 50% of the intensity values are located within the window W). The bright areas indicate the pixels included. As can be seen, the area with the included pixels need not be contiguous.

Figure 5:
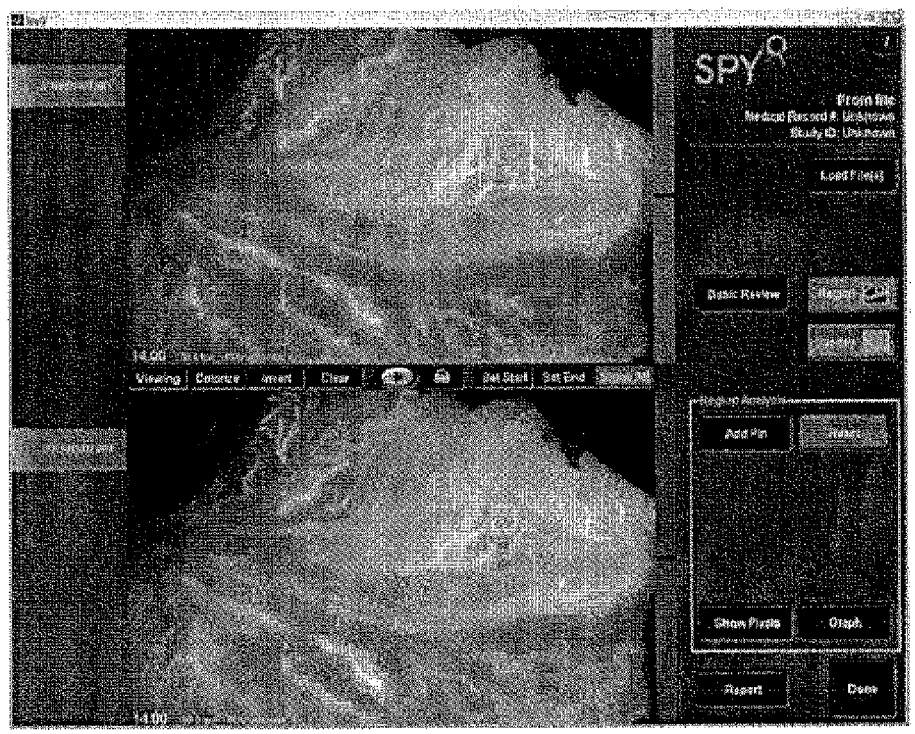
FIG. 5 shows the static ROI of FIG. 2 (top image) and a smaller static ROI (bottom image) located within the ROI of the top image.

FIG. 5 shows the static ROI of FIG. 2 (top image) and a smaller static ROI (bottom image) located within the ROI of the top image. The smaller ROI includes less arterial blood vessels.

Figure 6:
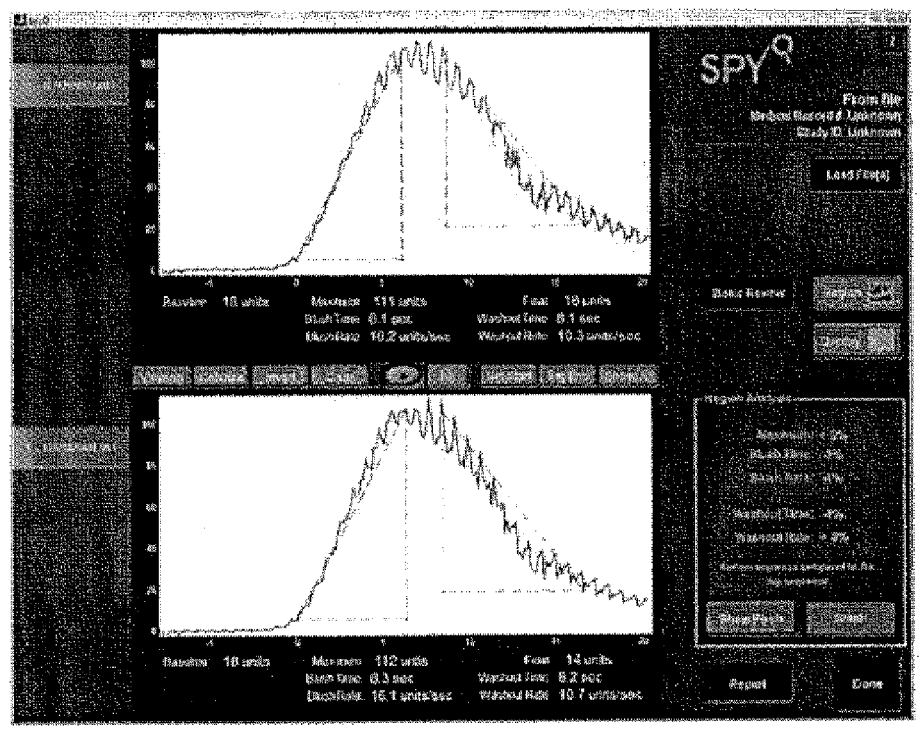
FIG. 6 shows the time dependence of the computed average intensity for the pixels highlighted in FIG. 4 (top image) and for the smaller static ROI of FIG. 5 (bottom image) taken over a 28 second time period.

FIG. 6 shows schematically the computed average intensity for both the static ROIs of FIG. 5 taken over a 28 second time interval. The elapsed time (from the point an increase in the intensity was detected, in seconds) is plotted on the abscissa, and the average intensity for the static ROI (in arbitrary units) is plotted on the ordinate. The two curves match within about 1-3 percent.

The maximum blush is approximately 112 [arb. units], the blush rate measured over about 6.1 sec from about zero blush to about the maximum value is in linear approximation about 16.2 [arb. units]/sec, and the washout rate measured over about 6.1 sec from about the maximum blush value to about 15-20% blush is in linear approximation about 10.5 [arb. units]/sec. Blush appears to increase and decrease (washout) exponentially, so the linear curve fitting described above should be considered only as an approximation, Other characteristic values of the curves of FIG. 6, such as a maximum slope or a curve fit with an exponential rise and decay time may also be used.

The average blush and the blush and washout rates obtained with this technique agree with the blush values perceived by the naked eye.

The static ROI algorithm described above does not rely on image tracking and is generally insensitive to the motion artifacts because of the exclusion of outliers. It is computationally fast and works well with both low and high contrast images.

Figure 7:
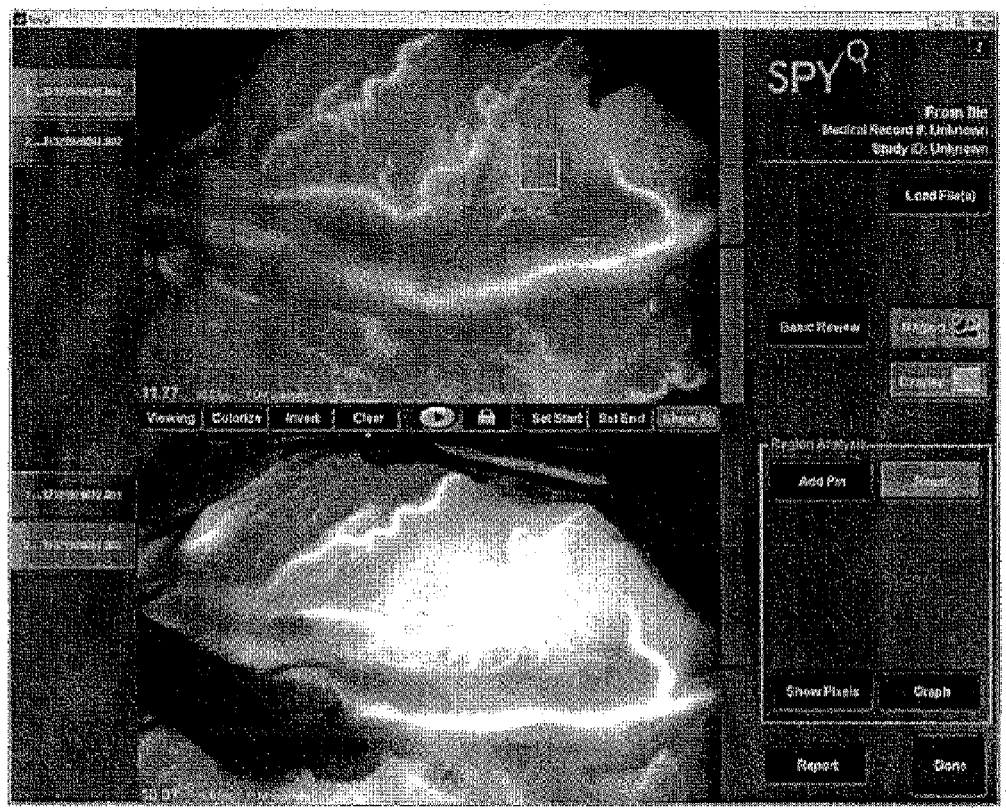
FIG. 7 shows an ICG fluorescent cardiac image with a static ROI before a surgical procedure (top image), and after the procedure (bottom image)

FIG. 7 shows pictures of the heart before and after a surgical procedure has been performed on the heart. A comparison of the blush determined with the aforedescribed method of the invention before and after the procedure can be used to determine whether perfusion has improved as a result of the procedure.

For obtaining reliable and meaningful results, the ICG dosage, illumination level and camera sensitivity settings should be adjusted so that the detector in the camera does not saturate when areas in the image, such as arteries, reach their maximum intensity. If the camera nevertheless does saturate, the user needs to decide whether the computed blush rate and washout rate are likely to represent the actual rates, had the detector not saturated.

Two approaches are proposed for comparing image data obtained before and after the procedure: (1) comparing the blush and washout rates before and after the procedure; and (2) comparing the elapsed time from blood vessel peak intensity to maximum blush on images taken before and after the procedure.

With the first approach, a time series of fluorescence images of the anatomy is acquired before (top image of FIG. 7) and after the surgical procedure (bottom image of FIG. 7) by, for example, injecting a bolus of ICG dye. Only one of the time series of images is shown. A ROI is delineated in each of the images in approximately the same area of the anatomy. The average intensity of the blush is then determined in each of, or in a subset of, the fluorescence images in the time series with the method of the invention described above with reference to the histogram of FIG. 3, which excludes outliers, such as arteries. The average ROI intensity from each image in the time series is normalized to the baseline average intensity of the ROI in the first frame to correct for residual ICG that may have remained in the system.

Figure 8:
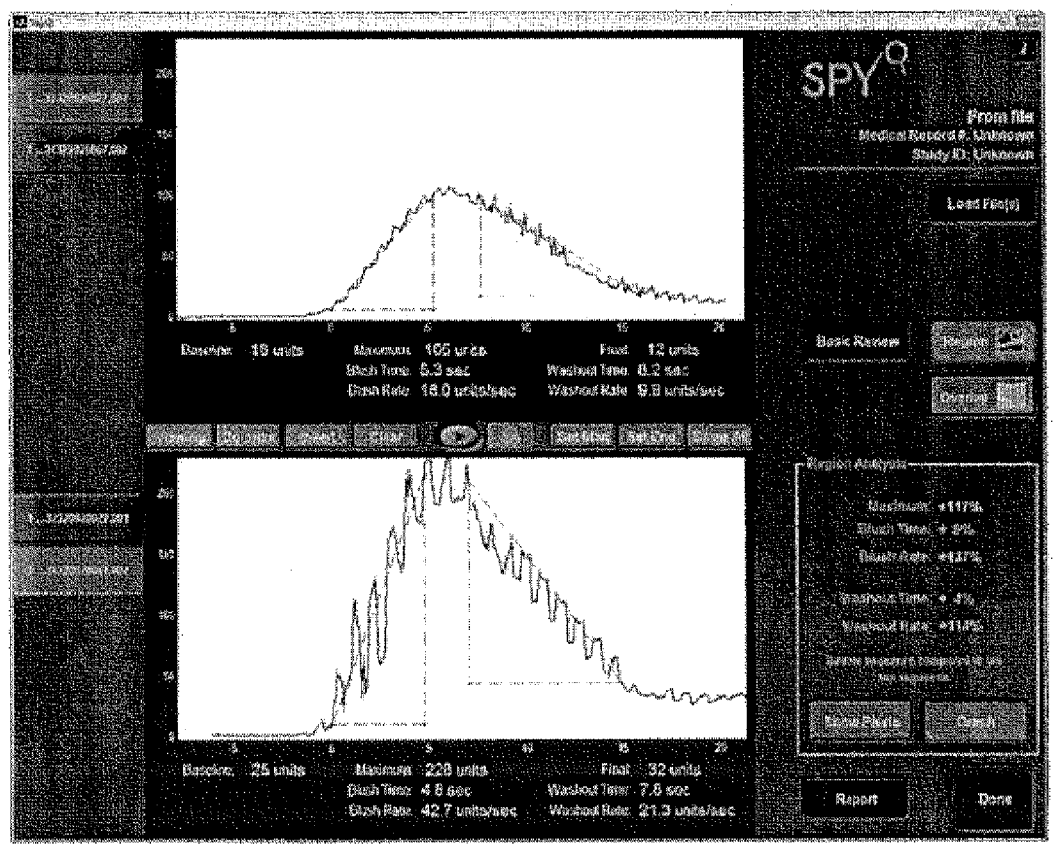
FIG. 8 shows the time evolution of the average blush intensity for the pixels within the ROI of FIG. 7 before the procedure (top image) and after the procedure (bottom image) taken over a 28 second time period.

FIG. 8 shows schematically the computed average intensities (about 50% of the intensity values are located within the window W of a histogram corresponding to the histogram of FIG. 3) for the static ROIs of FIG. 7 taken over a 28 second time interval. The top graph represents values before the procedure and the bottom graph values after the procedure. The elapsed time (from the point an increase in the intensity was detected, in seconds) is plotted on the abscissa, and the average intensity for the static ROI (in arbitrary units) is plotted on the ordinate. The broken line through the data represents a smoothed curve of the raw data. This helps to mask variation in the measurement due to motion caused by the cardiac cycle or respiration and serves as a visual guide for assessing the blush rate and washout rate. As mentioned above, saturation of the sensor should be avoided, because saturation would make an absolute determination of the slope impractical.

The blush and washout rates are determined from the corresponding slopes of straight lines connecting the 5% and 95% points in the average intensity curves, i.e., the start of blush is taken as the time at which the intensity rises above the baseline by 5% of its maximum value, and the 95% point is the time at which the intensity reaches 95% of its maximum value. The same applies to the determination of the washout rate, with the 5% point at the end of washout determined with reference to the final values, which may be higher than the initial 5% point due to residual IeG remaining in the myocardial tissue. The 5% and 95% thresholds are heuristic thresholds used to discount for any noise that may appear in the image both before the blush appears, and as it nears its maximum value.

It will be understood that the slope of the straight lines represents an average rate, and that the rate can also be determined from a least-square curve fit or by selecting points other than 5% and 95%, as described in the illustrated example.

As indicated in FIG. 8, the blush rate following the procedure is about 43 units/sec, compared to about 18 units/sec before the procedure, representing an improvement of about 140%. Likewise, the washout rate following the procedure is about 21 units/sec, compared to about 10 units/sec before the procedure, representing an improvement of more than 100%. Greater perfusion (blush) and washout rates suggest faster movement of blood and greater maximum blush suggests a greater volume of ICG-bound blood in the tissue and are hence clear indicators of improved perfusion through the tissue.

With the second approach, perfusion is determined from the time of maximum blood vessel (artery) intensity to maximum myocardial blush. For example, for cardiac surgery, the surgeon would draw two regions of interest (ROI), a first region covering the coronary artery feeding blood to the heart and a second region covering myocardial tissue receiving blood from that artery. The maximum myocardial blush is determined from the histogram of the first region, as described above (FIG. 8). Peak intensity of the blood vessel may advantageously be determined from an area in the first region showing pixel intensity greater than that of the surrounding tissue. For example, a histogram of the grayscale intensity values may be constructed for the first region and a sliding window W applied across the abscissa, wherein the smallest set of adjacent histogram bins containing a predetermined percentage, for example about 20%, of the pixels with the highest intensity. The lower percentage of pixels included in the computation of the average blood vessel intensity than for myocardial tissue gives the user some flexibility in drawing a larger ROI over the vessel to make the result less sensitive to lateral movement in the vessel during image acquisition.

It will be understood that the first and second regions need not be separate, but may 20 overlap or even be identical, as long as the fluorescence signals from the blood vessels and the myocardial tissue can be clearly separated in the histogram.

It has been observed that before the procedure, the myocardial area may reach maximum blush two seconds after the coronary artery reaches maximum fluorescence intensity. After the procedure, it may only take one second for the myocardial blush to reach maximum blush after the coronary artery reaches maximum fluorescence intensity following the vessel reaching maximum. This finding would lead to the conclusion that cardiac function has improved.

As mentioned above, a blood vessel may move laterally during image acquisition which may make it more difficult to reliably determine the fluorescence intensity, for example during ICG imaging, of a coronary artery. The proposed method provides a means for tracking the movement of the vessel by determining several, typically three, lines which follow the contour of a segment of interest of the blood vessel and approximately span the width of the vessel.

According to the method, features or edges in the image are determined by filtering using a convolution with the Laplacian-of-a-Gaussian kernel. The detected edges may be enhanced (thickened) by defining the edge by a width of at least two pixels. Both the original and the edge-enhanced images are stored.

Figure 9:
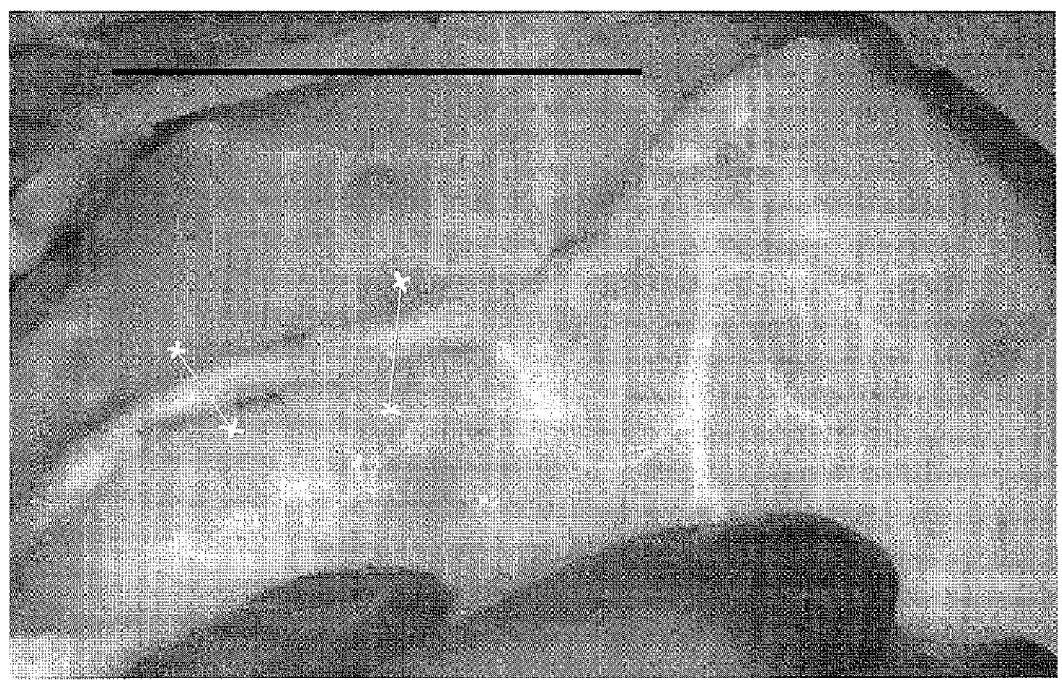
FIG. 9 shows delineation of a segment of a blood vessel for analysis with the method of the invention.
Figure 10:
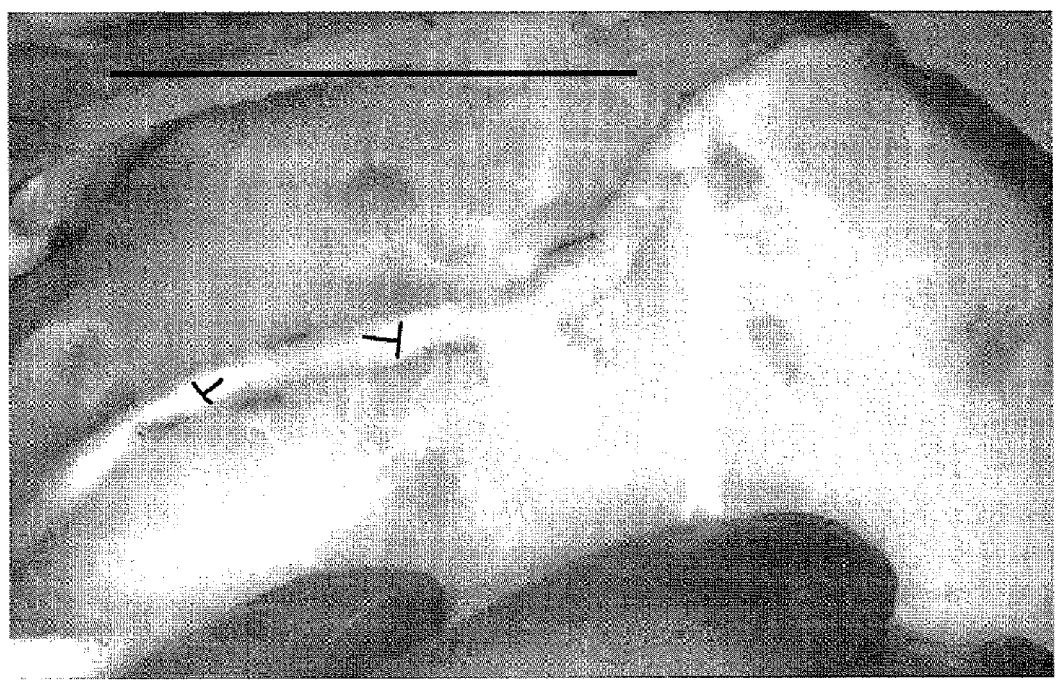
FIG. 10 shows the delineated segment of FIG. 9 with lines terminating at the vessel walls and line normals at the longitudinal end points.
Figure 11:
FIG. 11 shows the vessel walls and line normals at the longitudinal end points of FIG. 10 with proper orientation.

Referring now to FIGS. 9 and 10, an operator delimits the segment of the vessel of interest by drawing two lines across the vessel, for example with a computer mouse (FIG. 9). The system then uses the previously determined edge information to detect the segment of each line located between the vessel edges and the mid-point of that segment, which is necessarily also the mid-point of the vessel, and constructs a line normal to each line segment (FIG. 10). Thereafter, the system aligns two line normals with the major longitudinal axis of the vessel (FIG. 11).

Figure 12:
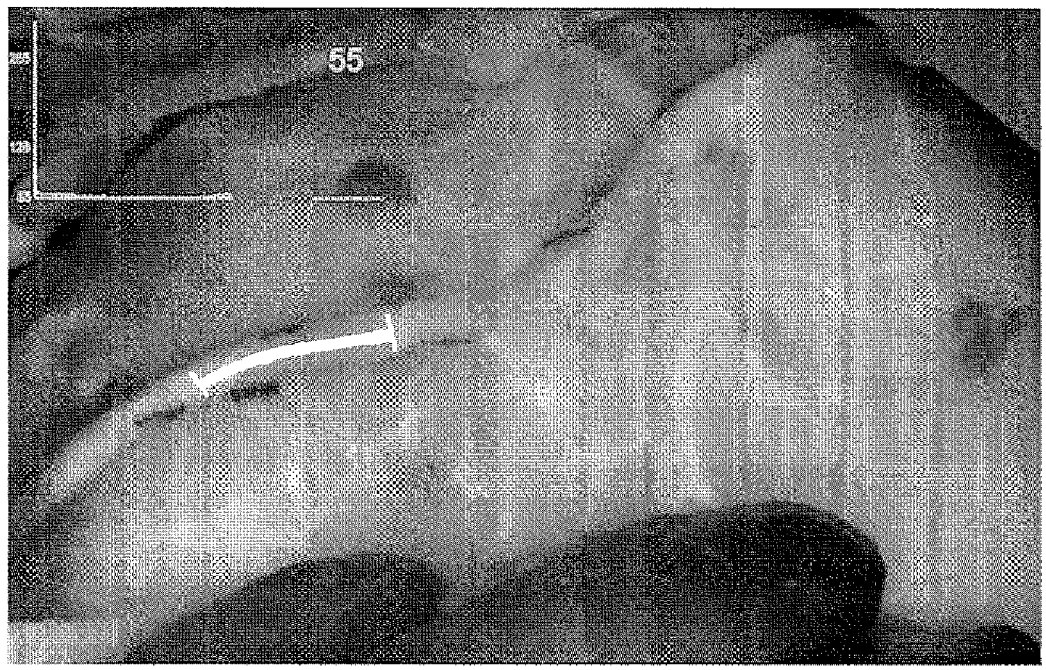
FIG. 12 shows splines connecting the longitudinal end points of FIG. 11 and a longitudinal intensity profile (upper left corner) taken before a procedure.

Next, the system constructs a series of 3 parallel lines, for example cubic spline, of approximately equal length joining the two ends of the segment of interest. However, a greater or lesser number of lines can be used. The lines have at their respective end points the same slope as the respective line normals. Three exemplary lines which approximately span the width of the vessel are shown in FIG. 12. The pixel intensity is sampled at points of each line along the longitudinal axis of the vessel. Preferably, intensities are averaged across the three lines at each location along the longitudinal axis to produce an average vessel intensity at each location in the vessel. As indicated in the insert at the top left corner of FIG. 12, the average intensity in the vessel segment is approximately 55, substantially independent of the longitudinal location in the vessel.

The process is then repeated for the time series of images frame-by-frame, while making sure that the positions match from one frame to the next.

Figure 13:
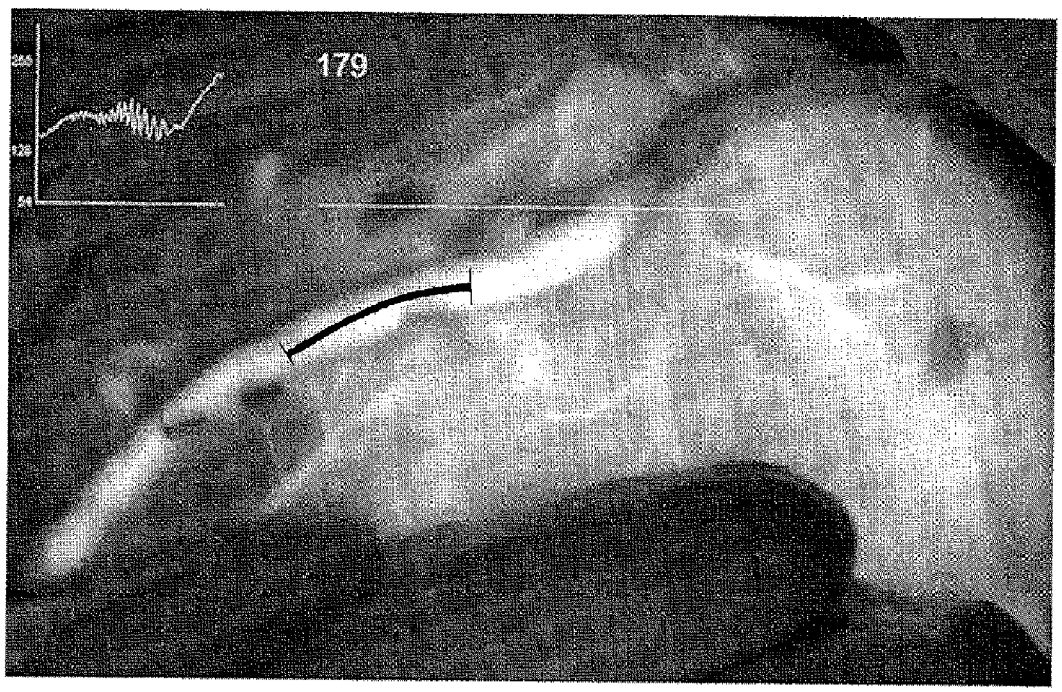
FIG. 13 shows splines connecting the longitudinal end points together with a longitudinal intensity profile (upper left corner) and the time dependence of the intensity profile (upper right corner) taken after a procedure.

FIG. 13 illustrates a final frame in the image sequence processed in this manner. The insert at the top left corner of FIG. 13 shows, as in FIG. 12, the averaged pixel intensity along the three lines. The segment now fluoresces noticeably stronger with an average intensity in the vessel segment of approximately 179. The insert at the top right corner of FIG. 13 shows the change in the average intensity for all of the processed time-ordered frame sequence of images. The "fill time" of the blood vessel can be calculated from the slope of the latter curve (pixel intensity vs. time).

The preceding concepts can be extended to develop quantitative indices useful for intraoperative assessment of blood flow in surgical flaps and for identifying vascular compromise.

Assuming that there is a peak having maximum fluorescence, the following metrics can be computed from the image sequence. If there is no peak, there is likely total arterial occlusion in the flap.

$I'_{In}$ is a measure for the rate of change of increasing perfusion with time as evidenced by the rate of ICG ingress or wash-in.

$I'_{Out}$ is a measure for the rate of change of decreasing perfusion with time after reaching maximum fluorescence intensity as evidenced by the rate of ICG egress or wash-out.

Each of the measures may be taken on a flap either pre- and post-operatively or, once the flap is in place, the measures may be taken from the flap and from adjacent native tissue.

With $I'_{in-Pre}$ being the rate of ICG ingress measured on either adjacent native tissue or on the flap pre-operatively, $I'_{in-Post}$ being the rate of ICG ingress measured on the flap post-operatively, Similarly, $I'_{Out-Pre}$ being the rate of ICG egress measured on either adjacent native tissue or on the flap pre-operatively, and $I'_{Out-Post}$ being the rate of ICG egress measured on the flap post-operatively, the Wash-in Ratio $WR_{In}$ can be defined as:

$$WR_{in} = I'_{in-Post}/I'_{in-Pre}$$

and the Wash-out Ratio $WR_{Out}$ can be defined as:

$$WR_{out} = I'_{Out-Post}/I'_{Out-Pre}.$$

$WR_{In}$ and $WR_{Out}$ will be close to 1.0 in cases with normal vascular conditions.

$WR_{In}$ will be significantly less than 1.0 in cases of arterial spasm or partial arterial occlusion. This metric will vary inversely to the degree of arterial spasm or partial arterial occlusion; the amount by which this metric is less than 1.0 will correlate with increased arterial spasm or arterial occlusion.

$WR_{Out}$ will be significantly less than 1.0 in cases of venous congestion. This metric will vary inversely to the degree of venous congestion; the amount by which this metric is less than 1.0 will correlate with increased venous congestion.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling within the spirit and scope of the appended claims.

What is claimed is:

1. A method for tracking a blood vessel in an image, comprising the steps of:
   (a) acquiring a fluorescence image of tissue containing a blood vessel;
   (b) delimiting a segment of the blood vessel with boundaries oriented substantially perpendicular to a longitudinal direction of the blood vessel;
   (c) constructing at least one curve extending between the delimiting boundaries and located within lateral vessel walls of the blood vessel, wherein the at least one curve terminates at the delimiting boundaries substantially perpendicular to the boundaries; and
   (d) determining a fluorescence signal intensity in the fluorescence image along the at least one curve, with the signal intensity being representative of vessel perfusion.

2. The method of claim 1, wherein the at least one curve is defined by a spline function.

3. The method of claim 1, wherein constructing at least one curve includes constructing a plurality of curves and determining the fluorescence signal intensity includes averaging the signal intensity from points on the plurality of curves having a substantially identical distance from one of the delimiting boundaries.

4. The method of claim 1, wherein a position of the lateral vessel walls in the fluorescence image is detected by an edge-detection algorithm.

5. The method of claim 4, wherein the edge-detection algorithm is implemented with a Laplacian-of-a-Gaussian operator.

6. The method of claim 4, further comprising the steps of:
   acquiring time-sequential fluorescence images of the tissue containing the blood vessel;
   determining characteristic dimensions of the delimited segment from the location of the lateral vessel walls in a first image;
   determining positions of lateral vessel walls in at least one second image;
   matching the characteristic dimensions from the first image to the positions of lateral vessel walls in the second image to find a location of the lateral vessel walls of the first image in the at least one second image; and
   repeating steps (c) and (d) for the at least one second image.

7. The method of claim 6, further comprising:
   computing an average fluorescence signal intensity of all points along the curve, and
   determining a change in perfusion of the blood vessel from a change in the average fluorescence signal intensity between the time-sequential images.

* * * * *